US007001882B1

(12) United States Patent
Schlehuber

(10) Patent No.: US 7,001,882 B1
(45) Date of Patent: Feb. 21, 2006

(54) MUTEINS OF BILIN-BINDING PROTEIN

(75) Inventor: Steffen Schlehuber, Freising (DE)

(73) Assignee: Pieris Proteolab AG, Freising-Weihenstephan (DE)

( * ) Notice: Subject to any disclaimer, the term of this patent is extended or adjusted under 35 U.S.C. 154(b) by 280 days.

(21) Appl. No.: 09/980,862

(22) PCT Filed: Jun. 8, 2000

(86) PCT No.: PCT/DE00/01873

§ 371 (c)(1),
(2), (4) Date: Feb. 27, 2002

(87) PCT Pub. No.: WO00/75308

PCT Pub. Date: Dec. 14, 2000

(30) Foreign Application Priority Data

Jun. 8, 1999 (DE) ................................ 199 26 068

(51) Int. Cl.
*C07K 14/00* (2006.01)
*C12N 15/00* (2006.01)

(52) U.S. Cl. .............................. 514/8; 514/2; 530/350; 530/395; 530/378.3; 435/69.7; 435/440

(58) Field of Classification Search ................... 514/8, 514/2; 530/350, 395, 378.3; 435/69.7, 440
See application file for complete search history.

(56) References Cited

FOREIGN PATENT DOCUMENTS

| EP | 0 835 934 | 4/1998 |
| WO | 89/06698 | 7/1989 |
| WO | 99/16873 | 4/1999 |

OTHER PUBLICATIONS

Beste et al., "Small Antibody-Like Proteins with Prescribed Ligand Specificities Derived From the Lipocalin Fold," Biochemistry, Proceeding of the National Academy of Science of the United States, vol. 96, No. 5, pp. 1898-1903, Mar. 2, 1999.
Flower, "The Lipocalin Protein Family: Structure and Function," Biochemical Journal, vol. 318, pp. 1-14, 1996.
Schmidt et al, "The Bilin-Binding Protein of *Pieris brassicae* cDNA Sequence and Regulation of Expression Reveal Distinct Features of this Insect Pigment Protein," European Journal of Biochemistry, vol. 219, No. 3, FEBS, pp. 855-863, 1994.
Schlehuber et al., "A Novel Type of Receptor Protein, Based on the Lipocalin Scaffold, with Specificity for Digoxigenin," Journal of Molecular Biology, vol. 297, No. 5, Academic Press, pp. 1105-1120, Apr. 14, 2000.

*Primary Examiner*—Karen Cochrane Carlson
*Assistant Examiner*—Samuel Wei Liu
(74) *Attorney, Agent, or Firm*—Foley & Lardner LLP

(57) ABSTRACT

The present invention relates to muteins of the bilin-binding protein with binding activity to digoxigenin and to fusion proteins of such muteins, a method for preparing said muteins and fusion proteins thereof and their utilization for detecting or binding digoxigenin-labeled biomolecules. The invention especially relates to a polypeptide selected from muteins of the bilin-binding protein, characterized in that (a) it can bind digoxigenin or digoxigenin conjugates, (b) it does not bind ouabain, testosterone, and 4-aminofluorescein and (c) at least one of the sequence positions 28, 31, 34, 35, 36, 37, 58, 60, 69, 88, 90, 95, 97, 114, 116, 125, and 127 of the bilin-binding protein has an amino acid substitution. Due to their simple molecular structure, the inventive muteins provide advantages for production and utilization in comparison with antibodies against the digoxigenin group.

9 Claims, 4 Drawing Sheets

SEQUENCE LISTING

```
<160> NUMBER OF SEQ ID NOS: 29

<210> SEQ ID NO 1
<211> LENGTH: 1219
<212> TYPE: DNA
<213> ORGANISM: Artificial Sequence
<220> FEATURE:
<223> OTHER INFORMATION: Description of Artificial Sequence: Synthetic
      pBBP20 nucleic acid sequence
<220> FEATURE:
<221> NAME/KEY: CDS
<222> LOCATION: (22)..(1209)
<220> FEATURE:
<221> NAME/KEY: sig_peptide
<222> LOCATION: (22)..(84)
<220> FEATURE:
<221> NAME/KEY: mat_peptide
<222> LOCATION: (85)..(1209)
<223> OTHER INFORMATION: fusion protein of bilin-binding protein,
      Strep-tag II and fragment of phage coat protein pIII
<220> FEATURE:
<221> NAME/KEY: misc_feature
<222> LOCATION: (85)..(606)
<223> OTHER INFORMATION: mature bilin-binding protein
<220> FEATURE:
<221> NAME/KEY: misc_feature
<222> LOCATION: (607)..(636)
<223> OTHER INFORMATION: Strep-tag II-affinity tag
<220> FEATURE:
<221> NAME/KEY: misc_feature
<222> LOCATION: (637)..(639)
<223> OTHER INFORMATION: amber stop codon
<220> FEATURE:
<221> NAME/KEY: misc_feature
<222> LOCATION: (640)..(1209)
<223> OTHER INFORMATION: amino acids 217-406 of coat protein pIII

<400> SEQUENCE: 1
```

-continued

| | |
|---|---|
| tctagttaac gagggcaaaa a atg aaa aag aca gct atc gcg att gca gtg<br>                                       Met Lys Lys Thr Ala Ile Ala Ile Ala Val<br>                                       -20                  -15 | 51 |
| gca ctg gct ggt ttc gct acc gta gcg cag gcc gac gtg tac cac gac<br>Ala Leu Ala Gly Phe Ala Thr Val Ala Gln Ala Asp Val Tyr His Asp<br>    -10              -5                  -1  1                 5 | 99 |
| ggt gcc tgt ccc gaa gtc aag cca gtc gac aac ttc gac tgg tcc cag<br>Gly Ala Cys Pro Glu Val Lys Pro Val Asp Asn Phe Asp Trp Ser Gln<br>          10                    15                 20 | 147 |
| tac cat ggt aaa tgg tgg gaa gtc gcc aaa tac ccc aac tca gtt gag<br>Tyr His Gly Lys Trp Trp Glu Val Ala Lys Tyr Pro Asn Ser Val Glu<br>         25                    30                 35 | 195 |
| aag tac gga aag tgc gga tgg gct gag tac act cct gaa ggc aag agt<br>Lys Tyr Gly Lys Cys Gly Trp Ala Glu Tyr Thr Pro Glu Gly Lys Ser<br>     40                   45                50 | 243 |
| gtc aaa gtt tcg aac tac cac gta atc cac ggc aag gaa tac ttt att<br>Val Lys Val Ser Asn Tyr His Val Ile His Gly Lys Glu Tyr Phe Ile<br> 55                   60                65 | 291 |
| gaa gga act gcc tac cca gtt ggt gac tcc aag att gga aag atc tac<br>Glu Gly Thr Ala Tyr Pro Val Gly Asp Ser Lys Ile Gly Lys Ile Tyr<br> 70                   75                80                 85 | 339 |
| cac agc ctg act tac gga ggt gtc acc aag gag aac gta ttc aac gta<br>His Ser Leu Thr Tyr Gly Gly Val Thr Lys Glu Asn Val Phe Asn Val<br>          90                    95                100 | 387 |
| ctc tcc act gac aac aag aac tac atc atc gga tac tac tgc aaa tac<br>Leu Ser Thr Asp Asn Lys Asn Tyr Ile Ile Gly Tyr Tyr Cys Lys Tyr<br>     105                    110               115 | 435 |
| gac gag gac aag aag gga cac caa gac ttc gtc tgg gtg ctc tcc aga<br>Asp Glu Asp Lys Lys Gly His Gln Asp Phe Val Trp Val Leu Ser Arg<br>         120                    125               130 | 483 |
| agc atg gtc ctt act ggt gaa gcc aag acc gct gtc gag aac tac ctt<br>Ser Met Val Leu Thr Gly Glu Ala Lys Thr Ala Val Glu Asn Tyr Leu<br>     135                    140               145 | 531 |
| atc ggc tcc cca gta gtc gac tcc cag aaa ctg gta tac agt gac ttc<br>Ile Gly Ser Pro Val Val Asp Ser Gln Lys Leu Val Tyr Ser Asp Phe<br>150                  155                160               165 | 579 |
| tct gaa gcc gcc tgc aag gtc aac aat agc aac tgg tct cac ccg cag<br>Ser Glu Ala Ala Cys Lys Val Asn Asn Ser Asn Trp Ser His Pro Gln<br>         170                    175               180 | 627 |
| ttc gaa aaa tag gct ggc ggc ggc tct ggt ggt ggt tct ggc ggc ggc<br>Phe Glu Lys Gln Ala Gly Gly Gly Ser Gly Gly Gly Ser Gly Gly Gly<br>     185                    190               195 | 675 |
| tct gag ggt ggt ggc tct gag ggt ggc ggt tct gag ggt ggc ggc tct<br>Ser Glu Gly Gly Gly Ser Glu Gly Gly Gly Ser Glu Gly Gly Gly Ser<br>         200                    205               210 | 723 |
| gag gga ggc ggt tcc ggt ggt ggc tct ggt tcc ggt gat ttt gat tat<br>Glu Gly Gly Gly Ser Gly Gly Gly Ser Gly Ser Gly Asp Phe Asp Tyr<br>     215                    220               225 | 771 |
| gaa aag atg gca aac gct aat aag ggg gct atg acc gaa aat gcc gat<br>Glu Lys Met Ala Asn Ala Asn Lys Gly Ala Met Thr Glu Asn Ala Asp<br>230                  235                240               245 | 819 |
| gaa aac gcg cta cag tct gac gct aaa ggc aaa ctt gat tct gtc gct<br>Glu Asn Ala Leu Gln Ser Asp Ala Lys Gly Lys Leu Asp Ser Val Ala<br>         250                    255               260 | 867 |
| act gat tac ggt gct gct atc gat ggt ttc att ggt gac gtt tcc ggc<br>Thr Asp Tyr Gly Ala Ala Ile Asp Gly Phe Ile Gly Asp Val Ser Gly<br>         265                    270               275 | 915 |
| ctt gct aat ggt aat ggt gct act ggt gat ttt gct ggc tct aat tcc<br>Leu Ala Asn Gly Asn Gly Ala Thr Gly Asp Phe Ala Gly Ser Asn Ser<br>         280                    285               290 | 963 |

```
caa atg gct caa gtc ggt gac ggt gat aat tca cct tta atg aat aat    1011
Gln Met Ala Gln Val Gly Asp Gly Asp Asn Ser Pro Leu Met Asn Asn
    295                 300                 305 ttc cgt caa tat tta cct tcc ctc cct caa tcg gtt gaa tgt cgc cct    1059
Phe Arg Gln Tyr Leu Pro Ser Leu Pro Gln Ser Val Glu Cys Arg Pro
310                 315                 320                 325 ttt gtc ttt ggc gct ggt aaa cca tat gaa ttt tct att gat tgt gac    1107
Phe Val Phe Gly Ala Gly Lys Pro Tyr Glu Phe Ser Ile Asp Cys Asp
                330                 335                 340 aaa ata aac tta ttc cgt ggt gtc ttt gcg ttt ctt tta tat gtt gcc    1155
Lys Ile Asn Leu Phe Arg Gly Val Phe Ala Phe Leu Leu Tyr Val Ala
            345                 350                 355 acc ttt atg tat gta ttt tct acg ttt gct aac ata ctg cgt aat aag    1203
Thr Phe Met Tyr Val Phe Ser Thr Phe Ala Asn Ile Leu Arg Asn Lys
        360                 365                 370 gag tct taataagctt                                                  1219
Glu Ser
    375

<210> SEQ ID NO 2
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, t, c, g, other or unknown
<220> FEATURE:
<221> NAME/KEY: modified_base
<222> LOCATION: (38)
<223> OTHER INFORMATION: a, t, c, g, other or unknown
<220> FEATURE:
<221> NAME/KEY: modified_base
<222> LOCATION: (41)..(42)
<223> OTHER INFORMATION: a, t, c, g, other or unknown
<220> FEATURE:
<221> NAME/KEY: modified_base
<222> LOCATION: (44)..(45)
<223> OTHER INFORMATION: a, t, c, g, other or unknown

<400> SEQUENCE: 2
ccatggtaaa tggtgggaag tcgccaaata ccccnnknms nnsnnkaagt acggaaagtg    60
cgga                                                                 64

<210> SEQ ID NO 3
<211> LENGTH: 71
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(20)
<223> OTHER INFORMATION: a, t, c, g, other or unknown
<220> FEATURE:
<221> NAME/KEY: modified_base
<222> LOCATION: (46)..(47)
<223> OTHER INFORMATION: a, t, c, g, other or unknown
<220> FEATURE:
<221> NAME/KEY: modified_base
<222> LOCATION: (52)..(53)
<223> OTHER INFORMATION: a, t, c, g, other or unknown

<400> SEQUENCE: 3
```

```
gggtaggcgg taccttcsnn aaagtattcc ttgccgtgga ttacmnngta snncgaaact    60
ttgacactct t                                                        71
```

<210> SEQ ID NO 4
<211> LENGTH: 74
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)..(28)
<223> OTHER INFORMATION: a, t, c, g, other or unknown
<220> FEATURE:
<221> NAME/KEY: modified_base
<222> LOCATION: (33)..(34)
<223> OTHER INFORMATION: a, t, c, g, other or unknown
<220> FEATURE:
<221> NAME/KEY: modified_base
<222> LOCATION: (42)..(43)
<223> OTHER INFORMATION: a, t, c, g, other or unknown
<220> FEATURE:
<221> NAME/KEY: modified_base
<222> LOCATION: (54)..(55)
<223> OTHER INFORMATION: a, t, c, g, other or unknown

<400> SEQUENCE: 4

```
ccaagattgg aaagatctac cacagcnnsa ctnnkggagg tnnsaccvvs gagnnkgtat    60
tcaacgtact ctcc                                                     74
```

<210> SEQ ID NO 5
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, t, c, g, other or unknown
<220> FEATURE:
<221> NAME/KEY: modified_base
<222> LOCATION: (26)..(27)
<223> OTHER INFORMATION: a, t, c, g, other or unknown
<220> FEATURE:
<221> NAME/KEY: modified_base
<222> LOCATION: (53)..(54)
<223> OTHER INFORMATION: a, t, c, g, other or unknown
<220> FEATURE:
<221> NAME/KEY: modified_base
<222> LOCATION: (59)..(60)
<223> OTHER INFORMATION: a, t, c, g, other or unknown

<400> SEQUENCE: 5

```
tctggagagc acccagacmn ngtcsnngtg tcccttcttg tcctcgtcgt asnngcamnn    60
gtatccgatg atgtagtt                                                 78
```

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
cttcgactgg tcccagtacc atggtaaatg gtggga                             36
```

-continued

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caccagtaag gaccatgctt ctggagagca cccagac                                37

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 8
agatctttcc aatcttggag tcaccaactg ggtaggcggt accttc                      46

<210> SEQ ID NO 9
<211> LENGTH: 793
<212> TYPE: DNA
<213> ORGANISM: Artificial Sequence
<220> FEATURE:
<223> OTHER INFORMATION: Description of Artificial Sequence: Fragment of
      synthetic pBBP22 nucleic acid sequence
<220> FEATURE:
<221> NAME/KEY: CDS
<222> LOCATION: (22)..(783)
<220> FEATURE:
<221> NAME/KEY: sig_peptide
<222> LOCATION: (22)..(84)
<220> FEATURE:
<221> NAME/KEY: mat_peptide
<222> LOCATION: (85)..(783)
<223> OTHER INFORMATION: fusion protein of bilin-binding protein,
      Strep-Tag II and albumin-binding domain
<220> FEATURE:
<221> NAME/KEY: misc_feature
<222> LOCATION: (85)..(606)
<223> OTHER INFORMATION: mature bilin-binding protein
<220> FEATURE:
<221> NAME/KEY: misc_feature
<222> LOCATION: (607)..(636)
<223> OTHER INFORMATION: Strep-Tag II affinity tag
<220> FEATURE:
<221> NAME/KEY: misc_feature
<222> LOCATION: (637)..(783)
<223> OTHER INFORMATION: albumin binding domain from Protein G

<400> SEQUENCE: 9
tctagataac gagggcaaaa a atg aaa aag aca gct atc gcg att gca gtg        51
                        Met Lys Lys Thr Ala Ile Ala Ile Ala Val
                            -20                 -15 gca ctg gct ggt ttc gct acc gta gcg cag gcc gac gtg tac cac gac        99
Ala Leu Ala Gly Phe Ala Thr Val Ala Gln Ala Asp Val Tyr His Asp
    -10                  -5              -1   1                 5 ggt gcc tgt ccc gaa gtc aag cca gtc gac aac ttc gac tgg tcc cag       147
Gly Ala Cys Pro Glu Val Lys Pro Val Asp Asn Phe Asp Trp Ser Gln
                10                  15                  20 tac cat ggt aaa tgg tgg gaa gtc gcc aaa tac ccc aac tca gtt gag       195
Tyr His Gly Lys Trp Trp Glu Val Ala Lys Tyr Pro Asn Ser Val Glu
            25                  30                  35 aag tac gga aag tgc gga tgg gct gag tac act cct gaa ggc aag agt       243
Lys Tyr Gly Lys Cys Gly Trp Ala Glu Tyr Thr Pro Glu Gly Lys Ser
        40                  45                  50

```
gtc aaa gtt tcg aac tac cac gta atc cac ggc aag gaa tac ttt att      291
Val Lys Val Ser Asn Tyr His Val Ile His Gly Lys Glu Tyr Phe Ile
 55                  60                  65 gaa gga act gcc tac cca gtt ggt gac tcc aag att gga aag atc tac      339
Glu Gly Thr Ala Tyr Pro Val Gly Asp Ser Lys Ile Gly Lys Ile Tyr
 70                  75                  80                  85 cac agc ctg act tac gga ggt gtc acc aag gag aac gta ttc aac gta      387
His Ser Leu Thr Tyr Gly Gly Val Thr Lys Glu Asn Val Phe Asn Val
                 90                  95                 100 ctc tcc act gac aac aag aac tac atc atc gga tac tac tgc aaa tac      435
Leu Ser Thr Asp Asn Lys Asn Tyr Ile Ile Gly Tyr Tyr Cys Lys Tyr
                105                 110                 115 gac gag gac aag aag gga cac caa gac ttc gtc tgg gtg ctc tcc aga      483
Asp Glu Asp Lys Lys Gly His Gln Asp Phe Val Trp Val Leu Ser Arg
            120                 125                 130 agc atg gtc ctt act ggt gaa gcc aag acc gct gtc gag aac tac ctt      531
Ser Met Val Leu Thr Gly Glu Ala Lys Thr Ala Val Glu Asn Tyr Leu
            135                 140                 145 atc ggc tcc cca gta gtc gac tcc cag aaa ctg gta tac agt gac ttc      579
Ile Gly Ser Pro Val Val Asp Ser Gln Lys Leu Val Tyr Ser Asp Phe
150                 155                 160                 165 tct gaa gcc gcc tgc aag gtc aac aat agc aac tgg tct cac ccg cag      627
Ser Glu Ala Ala Cys Lys Val Asn Asn Ser Asn Trp Ser His Pro Gln
                170                 175                 180 ttc gaa aaa cca gct agc ctg gct gaa gct aaa gtt ctg gct aac cgt      675
Phe Glu Lys Pro Ala Ser Leu Ala Glu Ala Lys Val Leu Ala Asn Arg
                185                 190                 195 gaa ctg gac aaa tac ggt gtt tcc gac tac tac aaa aac ctc atc aac      723
Glu Leu Asp Lys Tyr Gly Val Ser Asp Tyr Tyr Lys Asn Leu Ile Asn
            200                 205                 210 aac gct aaa acc gtt gaa ggt gtt aaa gct ctg atc gac gaa att ctc      771
Asn Ala Lys Thr Val Glu Gly Val Lys Ala Leu Ile Asp Glu Ile Leu
215                 220                 225 gca gca ctg ccg taataagctt                                           793
Ala Ala Leu Pro
230

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 10
gacggtgcct gtcccga                                                    17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 11
gactactggg gagccga                                                    17

<210> SEQ ID NO 12
<211> LENGTH: 522
<212> TYPE: DNA
```

```
<213> ORGANISM: Artificial Sequence
<220> FEATURE:
<223> OTHER INFORMATION: Description of Artificial Sequence: Synthetic
      DigA nucleic acid sequence
<220> FEATURE:
<221> NAME/KEY: CDS
<222> LOCATION: (1)..(522)
<223> OTHER INFORMATION: mutein DigA without fusion parts

<400> SEQUENCE: 12 gac gtg tac cac gac ggt gcc tgt ccc gaa gtc aag cca gtc gac aac      48
Asp Val Tyr His Asp Gly Ala Cys Pro Glu Val Lys Pro Val Asp Asn
 1               5                  10                  15 ttc gac tgg tcc cag tac cat ggt aaa tgg tgg gaa gtc gcc aaa tac      96
Phe Asp Trp Ser Gln Tyr His Gly Lys Trp Trp Glu Val Ala Lys Tyr
             20                  25                  30 ccc cat cac gag cgg aag tac gga aag tgc gga tgg gct gag tac act     144
Pro His His Glu Arg Lys Tyr Gly Lys Cys Gly Trp Ala Glu Tyr Thr
         35                  40                  45 cct gaa ggc aag agt gtc aaa gtt tcg cgc tac tct gta atc cac ggc     192
Pro Glu Gly Lys Ser Val Lys Val Ser Arg Tyr Ser Val Ile His Gly
     50                  55                  60 aag gaa tac ttt tcc gaa ggt acc gcc tac cca gtt ggt gac tcc aag     240
Lys Glu Tyr Phe Ser Glu Gly Thr Ala Tyr Pro Val Gly Asp Ser Lys
 65                  70                  75                  80 att gga aag atc tac cac agc tac act att gga ggt gtg acc cag gag     288
Ile Gly Lys Ile Tyr His Ser Tyr Thr Ile Gly Gly Val Thr Gln Glu
                 85                  90                  95 ggt gta ttc aac gta ctc tcc act gac aac aag aac tac atc atc gga     336
Gly Val Phe Asn Val Leu Ser Thr Asp Asn Lys Asn Tyr Ile Ile Gly
            100                 105                 110 tac ttt tgc tcg tac gac gag gac aag aag gga cac atg gac ttg gtc     384
Tyr Phe Cys Ser Tyr Asp Glu Asp Lys Lys Gly His Met Asp Leu Val
        115                 120                 125 tgg gtg ctc tcc aga agc atg gtc ctt act ggt gaa gcc aag acc gct     432
Trp Val Leu Ser Arg Ser Met Val Leu Thr Gly Glu Ala Lys Thr Ala
    130                 135                 140 gtc gag aac tac ctt atc ggc tcc cca gta gtc gac tcc cag aaa ctg     480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat             522
Val Tyr Ser Asp Phe Ser Glu Ala Ala Cys Lys Val Asn Asn
                165                 170

<210> SEQ ID NO 13
<211> LENGTH: 76
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, t, c, g, t, other or unknown
<220> FEATURE:
<221> NAME/KEY: modified_base
<222> LOCATION: (38)..(39)
<223> OTHER INFORMATION: a, t, c, g, t, other or unknown
<220> FEATURE:
<221> NAME/KEY: modified_base
<222> LOCATION: (47)..(48)
<223> OTHER INFORMATION: a, t, c, g, t, other or unknown
<220> FEATURE:
<221> NAME/KEY: modified_base
<222> LOCATION: (50)..(51)
<223> OTHER INFORMATION: a, t, c, g, t, other or unknown
```

```
<220> FEATURE:
<221> NAME/KEY: modified_base
<222> LOCATION: (53)..(54)
<223> OTHER INFORMATION: a, t, c, g, t, other or unknown
<220> FEATURE:
<221> NAME/KEY: modified_base
<222> LOCATION: (56)..(57)
<223> OTHER INFORMATION: a, t, c, g, t, other or unknown

<400> SEQUENCE: 13
ctggtcccag taccatggta aatggtggnn kgtcgccnnk tacccennkn nknnknnkaa       60 gtacggaaag tgcgga                                                      76

<210> SEQ ID NO 14
<211> LENGTH: 1219
<212> TYPE: DNA
<213> ORGANISM: Artificial Sequence
<220> FEATURE:
<223> OTHER INFORMATION: Description of Artificial Sequence: Fragment of
      synthetic pBBP24 nucleic acid sequence
<220> FEATURE:
<221> NAME/KEY: CDS
<222> LOCATION: (22)..(1209)
<220> FEATURE:
<221> NAME/KEY: sig_peptide
<222> LOCATION: (22)..(84)
<220> FEATURE:
<221> NAME/KEY: mat_peptide
<222> LOCATION: (85)..(1209)
<223> OTHER INFORMATION: fusion protein of bilin-binding protein,
      Strep-Tag II and fragment of phage coat protein pIII, with
      interrupted reading frame
<220> FEATURE:
<221> NAME/KEY: misc_feature
<222> LOCATION: (85)..(606)
<223> OTHER INFORMATION: mature bilin-binding protein with interrupted
      reading frame
<220> FEATURE:
<221> NAME/KEY: misc_feature
<222> LOCATION: (607)..(636)
<223> OTHER INFORMATION: Strep-Tag II affinity tag
<220> FEATURE:
<221> NAME/KEY: misc_feature
<222> LOCATION: (637)..(639)
<223> OTHER INFORMATION: amber stop codon
<220> FEATURE:
<221> NAME/KEY: misc_feature
<222> LOCATION: (640)..(1209)
<223> OTHER INFORMATION: amino acids 217-406 of coat protein pIII

<400> SEQUENCE: 14
tctagataac gagggcaaaa a atg aaa aag aca gct atc gcg att gca gtg         51
                       Met Lys Lys Thr Ala Ile Ala Ile Ala Val
                          -20                 -15 gca ctg gct ggt ttc gct acc gta gcg cag gcc gac gtg tac cac gac         99
Ala Leu Ala Gly Phe Ala Thr Val Ala Gln Ala Asp Val Tyr His Asp
   -10                 -5                  -1   1               5 ggt gcc tgt ccc gaa gtc aag cca gtc gac aac ttc gac tgg tcc cag        147
Gly Ala Cys Pro Glu Val Lys Pro Val Asp Asn Phe Asp Trp Ser Gln
               10                  15                  20 tac cat ggt aaa tgg tgg gaa gtc gcc aaa tac ccc aac tca gtt gag        195
Tyr His Gly Lys Trp Trp Glu Val Ala Lys Tyr Pro Asn Ser Val Glu
           25                  30                  35 aag tac gga aat taatga tgg gct gag tac act cct gaa ggc aag agt        243
Lys Tyr Gly Asn        Trp Ala Glu Tyr Thr Pro Glu Gly Lys Ser
           40                  45                  50 gtc aaa gtt tcg aac tac cac gta atc cac ggc aag gaa tac ttt att       291
Val Lys Val Ser Asn Tyr His Val Ile His Gly Lys Glu Tyr Phe Ile
           55                  60                  65
```

```
gaa gga act gcc tac cca gtt ggt gac tcc aag att gga aag atc tac      339
Glu Gly Thr Ala Tyr Pro Val Gly Asp Ser Lys Ile Gly Lys Ile Tyr
            70                  75                  80 cac agc ctg act tac gga ggt gtc acc aag gag aac gta ttc aac gta      387
His Ser Leu Thr Tyr Gly Gly Val Thr Lys Glu Asn Val Phe Asn Val
 85                  90                  95 ctc tcc act gac aac aag aac tac atc atc gga tac tac tgc aaa tac      435
Leu Ser Thr Asp Asn Lys Asn Tyr Ile Ile Gly Tyr Tyr Cys Lys Tyr
100                 105                 110                 115 gac gag gac aag aag gga cac caa gac ttc gtc tgg gtg ctc tcc aga      483
Asp Glu Asp Lys Lys Gly His Gln Asp Phe Val Trp Val Leu Ser Arg
                    120                 125                 130 agc atg gtc ctt act ggt gaa gcc aag acc gct gtc gag aac tac ctt      531
Ser Met Val Leu Thr Gly Glu Ala Lys Thr Ala Val Glu Asn Tyr Leu
            135                 140                 145 atc ggc tcc cca gta gtc gac tcc cag aaa ctg gta tac agt gac ttc      579
Ile Gly Ser Pro Val Val Asp Ser Gln Lys Leu Val Tyr Ser Asp Phe
            150                 155                 160 tct gaa gcc gcc tgc aag gtc aac aat agc aac tgg tct cac ccg cag      627
Ser Glu Ala Ala Cys Lys Val Asn Asn Ser Asn Trp Ser His Pro Gln
165                 170                 175 ttc gaa aaa tag gct ggc ggc ggc tct ggt ggt ggt tct ggc ggc ggc      675
Phe Glu Lys Gln Ala Gly Gly Gly Ser Gly Gly Gly Ser Gly Gly Gly
180                 185                 190                 195 tct gag ggt ggt ggc tct gag ggt ggc ggt tct gag ggt ggc ggc tct      723
Ser Glu Gly Gly Gly Ser Glu Gly Gly Gly Ser Glu Gly Gly Gly Ser
                    200                 205                 210 gag gga ggc ggt tcc ggt ggt ggc tct ggt tcc ggt gat ttt gat tat      771
Glu Gly Gly Gly Ser Gly Gly Gly Ser Gly Ser Gly Asp Phe Asp Tyr
            215                 220                 225 gaa aag atg gca aac gct aat aag ggg gct atg acc gaa aat gcc gat      819
Glu Lys Met Ala Asn Ala Asn Lys Gly Ala Met Thr Glu Asn Ala Asp
            230                 235                 240 gaa aac gcg cta cag tct gac gct aaa ggc aaa ctt gat tct gtc gct      867
Glu Asn Ala Leu Gln Ser Asp Ala Lys Gly Lys Leu Asp Ser Val Ala
245                 250                 255 act gat tac ggt gct gct atc gat ggt ttc att ggt gac gtt tcc ggc      915
Thr Asp Tyr Gly Ala Ala Ile Asp Gly Phe Ile Gly Asp Val Ser Gly
260                 265                 270                 275 ctt gct aat ggt aat ggt gct act ggt gat ttt gct ggc tct aat tcc      963
Leu Ala Asn Gly Asn Gly Ala Thr Gly Asp Phe Ala Gly Ser Asn Ser
                    280                 285                 290 caa atg gct caa gtc ggt gac ggt gat aat tca cct tta atg aat aat     1011
Gln Met Ala Gln Val Gly Asp Gly Asp Asn Ser Pro Leu Met Asn Asn
            295                 300                 305 ttc cgt caa tat tta cct tcc ctc cct caa tcg gtt gaa tgt cgc cct     1059
Phe Arg Gln Tyr Leu Pro Ser Leu Pro Gln Ser Val Glu Cys Arg Pro
            310                 315                 320 ttt gtc ttt ggc gct ggt aaa cca tat gaa ttt tct att gat tgt gac     1107
Phe Val Phe Gly Ala Gly Lys Pro Tyr Glu Phe Ser Ile Asp Cys Asp
            325                 330                 335 aaa ata aac tta ttc cgt ggt gtc ttt gcg ttt ctt tta tat gtt gcc     1155
Lys Ile Asn Leu Phe Arg Gly Val Phe Ala Phe Leu Leu Tyr Val Ala
340                 345                 350                 355 acc ttt atg tat gta ttt tct acg ttt gct aac ata ctg cgt aat aag     1203
Thr Phe Met Tyr Val Phe Ser Thr Phe Ala Asn Ile Leu Arg Asn Lys
                    360                 365                 370 gag tct taataagctt                                                   1219
Glu Ser
```

```
<210> SEQ ID NO 15
<211> LENGTH: 522
<212> TYPE: DNA
<213> ORGANISM: Artificial Sequence
<220> FEATURE:
<223> OTHER INFORMATION: Description of Artificial Sequence: Mutein DigA
      nucleic acid sequence
<220> FEATURE:
<221> NAME/KEY: CDS
<222> LOCATION: (1)..(522)
<223> OTHER INFORMATION: mutein DigA16 without fusion parts

<400> SEQUENCE: 15 gac gtg tac cac gac ggt gcc tgt ccc gaa gtc aag cca gtc gac aac      48
Asp Val Tyr His Asp Gly Ala Cys Pro Glu Val Lys Pro Val Asp Asn
  1               5                  10                  15 ttc gac tgg tcc cag tac cat ggt aaa tgg tgg cag gtc gcc gcg tac      96
Phe Asp Trp Ser Gln Tyr His Gly Lys Trp Trp Gln Val Ala Ala Tyr
             20                  25                  30 ccc gat cat att acg aag tac gga aag tgc gga tgg gct gag tac act     144
Pro Asp His Ile Thr Lys Tyr Gly Lys Cys Gly Trp Ala Glu Tyr Thr
         35                  40                  45 cct gaa ggc aag agt gtc aaa gtt tcg cgc tac tct gta atc cac ggc     192
Pro Glu Gly Lys Ser Val Lys Val Ser Arg Tyr Ser Val Ile His Gly
 50                  55                  60 aag gaa tac ttt tcc gaa ggt acc gcc tac cca gtt ggt gac tcc aag     240
Lys Glu Tyr Phe Ser Glu Gly Thr Ala Tyr Pro Val Gly Asp Ser Lys
 65                  70                  75                  80 att gga aag atc tac cac agc tac act att gga ggt gtg acc cag gag     288
Ile Gly Lys Ile Tyr His Ser Tyr Thr Ile Gly Gly Val Thr Gln Glu
                 85                  90                  95 ggt gta ttc aac gta ctc tcc act gac aac aag aac tac atc atc gga     336
Gly Val Phe Asn Val Leu Ser Thr Asp Asn Lys Asn Tyr Ile Ile Gly
            100                 105                 110 tac ttt tgc tcg tac gac gag gac aag aag gga cac atg gac ttg gtc     384
Tyr Phe Cys Ser Tyr Asp Glu Asp Lys Lys Gly His Met Asp Leu Val
        115                 120                 125 tgg gtg ctc tcc aga agc atg gtc ctt act ggt gaa gcc aag acc gct     432
Trp Val Leu Ser Arg Ser Met Val Leu Thr Gly Glu Ala Lys Thr Ala
130                 135                 140 gtc gag aac tac ctt atc ggc tcc cca gta gtc gac tcc cag aaa ctg     480
Val Glu Asn Tyr Leu Ile Gly Ser Pro Val Val Asp Ser Gln Lys Leu
145                 150                 155                 160 gta tac agt gac ttc tct gaa gcc gcc tgc aag gtc aac aat              522
Val Tyr Ser Asp Phe Ser Glu Ala Ala Cys Lys Val Asn Asn
                165                 170

<210> SEQ ID NO 16
<211> LENGTH: 1380
<212> TYPE: DNA
<213> ORGANISM: Artificial Sequence
<220> FEATURE:
<223> OTHER INFORMATION: Description of Artificial Sequence: Fragment of
      synthetic pBBP21 nucleic acid sequence
<220> FEATURE:
<221> NAME/KEY: CDS
<222> LOCATION: (22)..(636)
<220> FEATURE:
<221> NAME/KEY: sig_peptide
<222> LOCATION: (22)..(84)
<220> FEATURE:
<221> NAME/KEY: mat_peptide
<222> LOCATION: (85)..(636)
<223> OTHER INFORMATION: fusion protein of bilin-binding protein and
      Strep-Tag II
<220> FEATURE:
```

```
<221> NAME/KEY: CDS
<222> LOCATION: (658)..(1365)
<220> FEATURE:
<221> NAME/KEY: sig_peptide
<222> LOCATION: (658)..(717)
<220> FEATURE:
<221> NAME/KEY: mat_peptide
<222> LOCATION: (718)..(1365)
<223> OTHER INFORMATION: DsbC protein

<400> SEQUENCE: 16
```

| | | | | | | | | | | | | | | | |
|---|---|---|---|---|---|---|---|---|---|---|---|---|---|---|---|
| tctagataac gagggcaaaa a | atg | aaa | aag | aca | gct | atc | gcg | att | gca | gtg | | | | | 51 |
| | Met | Lys | Lys | Thr | Ala | Ile | Ala | Ile | Ala | Val | | | | | |
| | | -20 | | | | -15 | | | | | | | | | |
| gca | ctg | gct | ggt | ttc | gct | acc | gta | gcg | cag | gcc | gac | gtg | tac | cac | gac | 99 |
| Ala | Leu | Ala | Gly | Phe | Ala | Thr | Val | Ala | Gln | Ala | Asp | Val | Tyr | His | Asp |
| | -10 | | | | -5 | | | | -1 | 1 | | | | 5 | |
| ggt | gcc | tgt | ccc | gaa | gtc | aag | cca | gtc | gac | aac | ttc | gac | tgg | tcc | cag | 147 |
| Gly | Ala | Cys | Pro | Glu | Val | Lys | Pro | Val | Asp | Asn | Phe | Asp | Trp | Ser | Gln |
| | | | 10 | | | | | 15 | | | | | 20 | | |
| tac | cat | ggt | aaa | tgg | tgg | gaa | gtc | gcc | aaa | tac | ccc | aac | tca | gtt | gag | 195 |
| Tyr | His | Gly | Lys | Trp | Trp | Glu | Val | Ala | Lys | Tyr | Pro | Asn | Ser | Val | Glu |
| | | | 25 | | | | 30 | | | | | 35 | | | |
| aag | tac | gga | aag | tgc | gga | tgg | gct | gag | tac | act | cct | gaa | ggc | aag | agt | 243 |
| Lys | Tyr | Gly | Lys | Cys | Gly | Trp | Ala | Glu | Tyr | Thr | Pro | Glu | Gly | Lys | Ser |
| | | 40 | | | | | 45 | | | | | 50 | | | |
| gtc | aaa | gtt | tcg | aac | tac | cac | gta | atc | cac | ggc | aag | gaa | tac | ttt | att | 291 |
| Val | Lys | Val | Ser | Asn | Tyr | His | Val | Ile | His | Gly | Lys | Glu | Tyr | Phe | Ile |
| | 55 | | | | | 60 | | | | | 65 | | | | |
| gaa | gga | act | gcc | tac | cca | gtt | ggt | gac | tcc | aag | att | gga | aag | atc | tac | 339 |
| Glu | Gly | Thr | Ala | Tyr | Pro | Val | Gly | Asp | Ser | Lys | Ile | Gly | Lys | Ile | Tyr |
| 70 | | | | | 75 | | | | | 80 | | | | | 85 |
| cac | agc | ctg | act | tac | gga | ggt | gtc | acc | aag | gag | aac | gta | ttc | aac | gta | 387 |
| His | Ser | Leu | Thr | Tyr | Gly | Gly | Val | Thr | Lys | Glu | Asn | Val | Phe | Asn | Val |
| | | | | 90 | | | | | 95 | | | | | 100 | |
| ctc | tcc | act | gac | aac | aag | aac | tac | atc | atc | gga | tac | tac | tgc | aaa | tac | 435 |
| Leu | Ser | Thr | Asp | Asn | Lys | Asn | Tyr | Ile | Ile | Gly | Tyr | Tyr | Cys | Lys | Tyr |
| | | | 105 | | | | | 110 | | | | | 115 | | |
| gac | gag | gac | aag | aag | gga | cac | caa | gac | ttc | gtc | tgg | gtg | ctc | tcc | aga | 483 |
| Asp | Glu | Asp | Lys | Lys | Gly | His | Gln | Asp | Phe | Val | Trp | Val | Leu | Ser | Arg |
| | | 120 | | | | | 125 | | | | | 130 | | | |
| agc | atg | gtc | ctt | act | ggt | gaa | gcc | aag | acc | gct | gtc | gag | aac | tac | ctt | 531 |
| Ser | Met | Val | Leu | Thr | Gly | Glu | Ala | Lys | Thr | Ala | Val | Glu | Asn | Tyr | Leu |
| | 135 | | | | | 140 | | | | | 145 | | | | |
| atc | ggc | tcc | cca | gta | gtc | gac | tcc | cag | aaa | ctg | gta | tac | agt | gac | ttc | 579 |
| Ile | Gly | Ser | Pro | Val | Val | Asp | Ser | Gln | Lys | Leu | Val | Tyr | Ser | Asp | Phe |
| 150 | | | | | 155 | | | | | 160 | | | | | 165 |
| tct | gaa | gcc | gcc | tgc | aag | gtc | aac | aat | agc | aac | tgg | tct | cac | ccg | cag | 627 |
| Ser | Glu | Ala | Ala | Cys | Lys | Val | Asn | Asn | Ser | Asn | Trp | Ser | His | Pro | Gln |
| | | | | 170 | | | | | 175 | | | | | 180 | |
| ttc | gaa | aaa | taataagctt cgggaagatt t | atg | aag | aaa | ggt | ttt | atg | ttg | | | | | 678 |
| Phe | Glu | Lys | | Met | Lys | Lys | Gly | Phe | Met | Leu | | | | | |
| | | | | | -20 | | | | -15 | | | | | | |
| ttt | act | ttg | tta | gcg | gcg | ttt | tca | ggc | ttt | gct | cag | gct | gat | gac | gcg | 726 |
| Phe | Thr | Leu | Leu | Ala | Ala | Phe | Ser | Gly | Phe | Ala | Gln | Ala | Asp | Asp | Ala |
| | | -10 | | | | | -5 | | | | | -1 | 1 | | |
| gca | att | caa | caa | acg | tta | gcc | aaa | atg | ggc | atc | aaa | agc | agc | gat | att | 774 |
| Ala | Ile | Gln | Gln | Thr | Leu | Ala | Lys | Met | Gly | Ile | Lys | Ser | Ser | Asp | Ile |
| | 5 | | | | | 10 | | | | | 15 | | | | |
| cag | ccc | gcg | cct | gta | gct | ggc | atg | aag | aca | gtt | ctg | act | aac | agc | ggc | 822 |
| Gln | Pro | Ala | Pro | Val | Ala | Gly | Met | Lys | Thr | Val | Leu | Thr | Asn | Ser | Gly |
| 20 | | | | | 25 | | | | | 30 | | | | | 35 |

```
gtg ttg tac atc acc gat gat ggt aaa cat atc att cag ggg cca atg       870
Val Leu Tyr Ile Thr Asp Asp Gly Lys His Ile Ile Gln Gly Pro Met
             40                  45                  50 tat gac gtt agt ggc acg gct ccg gtc aat gtc acc aat aag atg ctg       918
Tyr Asp Val Ser Gly Thr Ala Pro Val Asn Val Thr Asn Lys Met Leu
         55                  60                  65 tta aag cag ttg aat gcg ctt gaa aaa gag atg atc gtt tat aaa gcg       966
Leu Lys Gln Leu Asn Ala Leu Glu Lys Glu Met Ile Val Tyr Lys Ala
     70                  75                  80 ccg cag gaa aaa cac gtc atc acc gtg ttt act gat att acc tgt ggt      1014
Pro Gln Glu Lys His Val Ile Thr Val Phe Thr Asp Ile Thr Cys Gly
 85                  90                  95 tac tgc cac aaa ctg cat gag caa atg gca gac tac aac gcg ctg ggg      1062
Tyr Cys His Lys Leu His Glu Gln Met Ala Asp Tyr Asn Ala Leu Gly
100                 105                 110                 115 atc acc gtg cgt tat ctt gct ttc ccg cgc cag ggg ctg gac agc gat      1110
Ile Thr Val Arg Tyr Leu Ala Phe Pro Arg Gln Gly Leu Asp Ser Asp
                120                 125                 130 gca gag aaa gaa atg aaa gct atc tgg tgt gcg aaa gat aaa aac aaa      1158
Ala Glu Lys Glu Met Lys Ala Ile Trp Cys Ala Lys Asp Lys Asn Lys
             135                 140                 145 gcg ttt gat gat gtg atg gca ggt aaa agc gtc gca cca gcc agt tgc      1206
Ala Phe Asp Asp Val Met Ala Gly Lys Ser Val Ala Pro Ala Ser Cys
         150                 155                 160 gac gtg gat att gcc gac cat tac gca ctt ggc gtc cag ctt ggc gtt      1254
Asp Val Asp Ile Ala Asp His Tyr Ala Leu Gly Val Gln Leu Gly Val
165                 170                 175 agc ggt act ccg gca gtt gtg ctg agc aat ggc aca ctt gtt ccg ggt      1302
Ser Gly Thr Pro Ala Val Val Leu Ser Asn Gly Thr Leu Val Pro Gly
180                 185                 190                 195 tac cag ccg ccg aaa gag atg aaa gaa ttc ctc gac gaa cac caa aaa      1350
Tyr Gln Pro Pro Lys Glu Met Lys Glu Phe Leu Asp Glu His Gln Lys
                200                 205                 210 atg acc agc ggt aaa taattcgcgt agctt                                 1380
Met Thr Ser Gly Lys
            215

<210> SEQ ID NO 17
<211> LENGTH: 2009
<212> TYPE: DNA
<213> ORGANISM: Artificial Sequence
<220> FEATURE:
<223> OTHER INFORMATION: Description of Artificial Sequence: Fragment of
      synthetic pBBP27 nucleic acid sequence
<220> FEATURE:
<221> NAME/KEY: CDS
<222> LOCATION: (23)..(1999)
<220> FEATURE:
<221> NAME/KEY: sig_peptide
<222> LOCATION: (23)..(85)
<220> FEATURE:
<221> NAME/KEY: mat_peptide
<222> LOCATION: (86)..(1999)
<223> OTHER INFORMATION: fusion protein of alkaline phosphatase, linker
      peptide Pro-Pro-Ser-Ala, mutein DigA16 and Strep-Tag II
<220> FEATURE:
<221> NAME/KEY: misc_feature
<222> LOCATION: (86)..(1435)
<223> OTHER INFORMATION: mature part of alkaline phosphatase
<220> FEATURE:
<221> NAME/KEY: misc_feature
<222> LOCATION: (1436)..(1447)
<223> OTHER INFORMATION: linker peptide Pro-Pro-Ser-Ala
<220> FEATURE:
<221> NAME/KEY: misc_feature
<222> LOCATION: (1448)..(1969)
```

-continued

```
<223> OTHER INFORMATION: mutein DigA16
<220> FEATURE:
<221> NAME/KEY: misc_feature
<222> LOCATION: (1970)..(1999)
<223> OTHER INFORMATION: Strep-Tag II affinity tag

<400> SEQUENCE: 17
tctagaacat ggagaaaata aa gtg aaa caa agc act att gca ctg gca ctc       52
                         Val Lys Gln Ser Thr Ile Ala Leu Ala Leu
                            -20                 -15 tta ccg tta ctg ttt acc cct gtg aca aaa gcc cgg aca cca gaa atg      100
Leu Pro Leu Leu Phe Thr Pro Val Thr Lys Ala Arg Thr Pro Glu Met
    -10                  -5              -1   1                5 cct gtt ctg gaa aac cgg gct gct cag ggc gat att act gca ccc ggc      148
Pro Val Leu Glu Asn Arg Ala Ala Gln Gly Asp Ile Thr Ala Pro Gly
                 10                  15                  20 ggt gct cgc cgt tta acg ggt gat cag act gcc gct ctg cgt gat tct      196
Gly Ala Arg Arg Leu Thr Gly Asp Gln Thr Ala Ala Leu Arg Asp Ser
             25                  30                  35 ctt agc gat aaa cct gca aaa aat att att ttg ctg att ggc gat ggg      244
Leu Ser Asp Lys Pro Ala Lys Asn Ile Ile Leu Leu Ile Gly Asp Gly
         40                  45                  50 atg ggg gac tcg gaa att act gcc gca cgt aat tat gcc gaa ggt gcg      292
Met Gly Asp Ser Glu Ile Thr Ala Ala Arg Asn Tyr Ala Glu Gly Ala
     55                  60                  65 ggc ggc ttt ttt aaa ggt ata gat gcc tta ccg ctt acc ggg caa tac      340
Gly Gly Phe Phe Lys Gly Ile Asp Ala Leu Pro Leu Thr Gly Gln Tyr
 70                  75                  80                  85 act cac tat gcg ctg aat aaa aaa acc ggc aaa ccg gac tac gtc acc      388
Thr His Tyr Ala Leu Asn Lys Lys Thr Gly Lys Pro Asp Tyr Val Thr
                 90                  95                 100 gac tcg gct gca tca gca acc gcc tgg tca acc ggt gtc aaa acc tat      436
Asp Ser Ala Ala Ser Ala Thr Ala Trp Ser Thr Gly Val Lys Thr Tyr
             105                 110                 115 aac ggc gcg ctg ggc gtc gat att cac gaa aaa gat cac cca acg att      484
Asn Gly Ala Leu Gly Val Asp Ile His Glu Lys Asp His Pro Thr Ile
         120                 125                 130 ctg gaa atg gca aaa gcc gca ggt ctg gcg acc ggt aac gtt tct acc      532
Leu Glu Met Ala Lys Ala Ala Gly Leu Ala Thr Gly Asn Val Ser Thr
     135                 140                 145 gca gag ttg cag gat gcc acg ccc gct gcg ctg gtg gca cat gtg acc      580
Ala Glu Leu Gln Asp Ala Thr Pro Ala Ala Leu Val Ala His Val Thr
150                 155                 160                 165 tcg cgc aaa tgc tac ggt ccg agc gcg acc agt gaa aaa tgt ccg ggt      628
Ser Arg Lys Cys Tyr Gly Pro Ser Ala Thr Ser Glu Lys Cys Pro Gly
                 170                 175                 180 aac gct ctg gaa aaa ggc gga aaa gga tcg att acc gaa cag ctg ctt      676
Asn Ala Leu Glu Lys Gly Gly Lys Gly Ser Ile Thr Glu Gln Leu Leu
             185                 190                 195 aac gct cgt gcc gac gtt acg ctt ggc ggc ggc gca aaa acc ttt gct      724
Asn Ala Arg Ala Asp Val Thr Leu Gly Gly Gly Ala Lys Thr Phe Ala
         200                 205                 210 gaa acg gca acc gct ggt gaa tgg cag gga aaa acg ctg cgt gaa cag      772
Glu Thr Ala Thr Ala Gly Glu Trp Gln Gly Lys Thr Leu Arg Glu Gln
     215                 220                 225 gca cag gcg cgt ggt tat cag ttg gtg agc gat gct gcc tca ctg aat      820
Ala Gln Ala Arg Gly Tyr Gln Leu Val Ser Asp Ala Ala Ser Leu Asn
230                 235                 240                 245 tcg gtg acg gaa gcg aat cag caa aaa ccc ctg ctt ggc ctg ttt gct      868
Ser Val Thr Glu Ala Asn Gln Gln Lys Pro Leu Leu Gly Leu Phe Ala
                 250                 255                 260
```

-continued

```
gac ggc aat atg cca gtg cgc tgg cta gga ccg aaa gca acg tac cat    916
Asp Gly Asn Met Pro Val Arg Trp Leu Gly Pro Lys Ala Thr Tyr His
            265                 270                 275 ggc aat atc gat aag ccc gca gtc acc tgt acg cca aat ccg caa cgt    964
Gly Asn Ile Asp Lys Pro Ala Val Thr Cys Thr Pro Asn Pro Gln Arg
        280                 285                 290 aat gac agt gta cca acc ctg gcg cag atg acc gac aaa gcc att gaa   1012
Asn Asp Ser Val Pro Thr Leu Ala Gln Met Thr Asp Lys Ala Ile Glu
    295                 300                 305 ttg ttg agt aaa aat gag aaa ggc ttt ttc ctg caa gtt gaa ggt gcg   1060
Leu Leu Ser Lys Asn Glu Lys Gly Phe Phe Leu Gln Val Glu Gly Ala
310                 315                 320                 325 tca atc gat aaa cag gat cat gct gcg aat cct tgt ggg caa att ggc   1108
Ser Ile Asp Lys Gln Asp His Ala Ala Asn Pro Cys Gly Gln Ile Gly
                330                 335                 340 gag acg gtc gat ctc gat gaa gcc gta caa cgg gcg ctg gaa ttc gct   1156
Glu Thr Val Asp Leu Asp Glu Ala Val Gln Arg Ala Leu Glu Phe Ala
            345                 350                 355 aaa aag gag ggt aac acg ctg gtc ata gtc acc gct gat cac gcc cac   1204
Lys Lys Glu Gly Asn Thr Leu Val Ile Val Thr Ala Asp His Ala His
        360                 365                 370 gcc agc cag att gtt gcg ccg gat acc aaa gct ccg ggc ctc acc cag   1252
Ala Ser Gln Ile Val Ala Pro Asp Thr Lys Ala Pro Gly Leu Thr Gln
    375                 380                 385 gcg cta aat acc aaa gat ggc gca gtg atg gtg atg agt tac ggg aac   1300
Ala Leu Asn Thr Lys Asp Gly Ala Val Met Val Met Ser Tyr Gly Asn
390                 395                 400                 405 tcc gaa gag gat tca caa gaa cat acc ggc agt cag ttg cgt att gcg   1348
Ser Glu Glu Asp Ser Gln Glu His Thr Gly Ser Gln Leu Arg Ile Ala
                410                 415                 420 gcg tat ggc ccg cat gcc gcc aat gtt gtt gga ctg acc gac cag acc   1396
Ala Tyr Gly Pro His Ala Ala Asn Val Val Gly Leu Thr Asp Gln Thr
            425                 430                 435 gat ctc ttc tac acc atg aaa gcc gct ctg ggg ctg aaa ccg cct agc   1444
Asp Leu Phe Tyr Thr Met Lys Ala Ala Leu Gly Leu Lys Pro Pro Ser
        440                 445                 450 gct gac gtg tac cac gac ggt gcc tgt ccc gaa gtc aag cca gtc gac   1492
Ala Asp Val Tyr His Asp Gly Ala Cys Pro Glu Val Lys Pro Val Asp
    455                 460                 465 aac ttc gac tgg tcc cag tac cat ggt aaa tgg tgg cag gtc gcc gcg   1540
Asn Phe Asp Trp Ser Gln Tyr His Gly Lys Trp Trp Gln Val Ala Ala
470                 475                 480                 485 tac ccc gat cat att acg aag tac gga aag tgc gga tgg gct gag tac   1588
Tyr Pro Asp His Ile Thr Lys Tyr Gly Lys Cys Gly Trp Ala Glu Tyr
                490                 495                 500 act cct gaa ggc aag agt gtc aaa gtt tcg cgc tac tct gta atc cac   1636
Thr Pro Glu Gly Lys Ser Val Lys Val Ser Arg Tyr Ser Val Ile His
            505                 510                 515 ggc aag gaa tac ttt tcc gaa ggt acc gcc tac cca gtt ggt gac tcc   1684
Gly Lys Glu Tyr Phe Ser Glu Gly Thr Ala Tyr Pro Val Gly Asp Ser
        520                 525                 530 aag att gga aag atc tac cac agc tac act att gga ggt gtg acc cag   1732
Lys Ile Gly Lys Ile Tyr His Ser Tyr Thr Ile Gly Gly Val Thr Gln
    535                 540                 545 gag ggt gta ttc aac gta ctc tcc act gac aac aag aac tac atc atc   1780
Glu Gly Val Phe Asn Val Leu Ser Thr Asp Asn Lys Asn Tyr Ile Ile
550                 555                 560                 565 gga tac ttt tgc tcg tac gac gag gac aag aag gga cac atg gac ttg   1828
Gly Tyr Phe Cys Ser Tyr Asp Glu Asp Lys Lys Gly His Met Asp Leu
```

```
                    570                 575                 580
gtc tgg gtg ctc tcc aga agc atg gtc ctt act ggt gaa gcc aag acc        1876
Val Trp Val Leu Ser Arg Ser Met Val Leu Thr Gly Glu Ala Lys Thr
                585                 590                 595 gct gtc gag aac tac ctt atc ggc tcc cca gta gtc gac tcc cag aaa        1924
Ala Val Glu Asn Tyr Leu Ile Gly Ser Pro Val Val Asp Ser Gln Lys
            600                 605                 610 ctg gta tac agt gac ttc tct gaa gcc gcc tgc aag gtc aac aat agc        1972
Leu Val Tyr Ser Asp Phe Ser Glu Ala Ala Cys Lys Val Asn Asn Ser
        615                 620                 625 aac tgg tct cac ccg cag ttc gaa aaa taataagctt                         2009
Asn Trp Ser His Pro Gln Phe Glu Lys
630                 635

<210> SEQ ID NO 18
<211> LENGTH: 2005
<212> TYPE: DNA
<213> ORGANISM: Artificial Sequence
<220> FEATURE:
<223> OTHER INFORMATION: Description of Artificial Sequence: Fragment of
      synthetic pBBP29 nucleic acid sequence
<220> FEATURE:
<221> NAME/KEY: CDS
<222> LOCATION: (22)..(1998)
<220> FEATURE:
<221> NAME/KEY: sig_peptide
<222> LOCATION: (22)..(84)
<220> FEATURE:
<221> NAME/KEY: mat_peptide
<222> LOCATION: (85)..(1998)
<223> OTHER INFORMATION: fusion protein of mutein DigA16, Strep-Tag II,
      linker peptide Gly(5) and alkaline phosphatase
<220> FEATURE:
<221> NAME/KEY: misc_feature
<222> LOCATION: (85)..(606)
<223> OTHER INFORMATION: mutein DigA16
<220> FEATURE:
<221> NAME/KEY: misc_feature
<222> LOCATION: (607)..(636)
<223> OTHER INFORMATION: Strep-Tag II affinity tag
<220> FEATURE:
<221> NAME/KEY: misc_feature
<222> LOCATION: (637)..(651)
<223> OTHER INFORMATION: linker peptide Gly-Gly-Gly-Gly-Gly
<220> FEATURE:
<221> NAME/KEY: misc_feature
<222> LOCATION: (652)..(1998)
<223> OTHER INFORMATION: alkaline phosphatase without signalling
      sequence and N-terminal Arg

<400> SEQUENCE: 18
tctagataac gagggcaaaa a atg aaa aag aca gct atc gcg att gca gtg         51
                        Met Lys Lys Thr Ala Ile Ala Ile Ala Val
                            -20                 -15 gca ctg gct ggt ttc gct acc gta gcg cag gcc gac gtg tac cac gac         99
Ala Leu Ala Gly Phe Ala Thr Val Ala Gln Ala Asp Val Tyr His Asp
    -10                  -5              -1   1                 5 ggt gcc tgt ccc gaa gtc aag cca gtc gac aac ttc gac tgg tcc cag        147
Gly Ala Cys Pro Glu Val Lys Pro Val Asp Asn Phe Asp Trp Ser Gln
                10                  15                  20 tac cat ggt aaa tgg tgg cag gtc gcc gcg tac ccc gat cat att acg        195
Tyr His Gly Lys Trp Trp Gln Val Ala Ala Tyr Pro Asp His Ile Thr
            25                  30                  35 aag tac gga aag tgc gga tgg gct gag tac act cct gaa ggc aag agt        243
Lys Tyr Gly Lys Cys Gly Trp Ala Glu Tyr Thr Pro Glu Gly Lys Ser
        40                  45                  50 gtc aaa gtt tcg cgc tac tct gta atc cac ggc aag gaa tac ttt tcc        291
Val Lys Val Ser Arg Tyr Ser Val Ile His Gly Lys Glu Tyr Phe Ser
```

-continued

```
                  55                  60                  65
gaa ggt acc gcc tac cca gtt ggt gac tcc aag att gga aag atc tac     339
Glu Gly Thr Ala Tyr Pro Val Gly Asp Ser Lys Ile Gly Lys Ile Tyr
 70                  75                  80                  85 cac agc tac act att gga ggt gtg acc cag gag ggt gta ttc aac gta     387
His Ser Tyr Thr Ile Gly Gly Val Thr Gln Glu Gly Val Phe Asn Val
                 90                  95                 100 ctc tcc act gac aac aag aac tac atc atc gga tac ttt tgc tcg tac     435
Leu Ser Thr Asp Asn Lys Asn Tyr Ile Ile Gly Tyr Phe Cys Ser Tyr
                105                 110                 115 gac gag gac aag aag gga cac atg gac ttg gtc tgg gtg ctc tcc aga     483
Asp Glu Asp Lys Lys Gly His Met Asp Leu Val Trp Val Leu Ser Arg
            120                 125                 130 agc atg gtc ctt act ggt gaa gcc aag acc gct gtc gag aac tac ctt     531
Ser Met Val Leu Thr Gly Glu Ala Lys Thr Ala Val Glu Asn Tyr Leu
        135                 140                 145 atc ggc tcc cca gta gtc gac tcc cag aaa ctg gta tac agt gac ttc     579
Ile Gly Ser Pro Val Val Asp Ser Gln Lys Leu Val Tyr Ser Asp Phe
150                 155                 160                 165 tct gaa gcc gcc tgc aag gtc aac aat agc aac tgg tct cac ccg cag     627
Ser Glu Ala Ala Cys Lys Val Asn Asn Ser Asn Trp Ser His Pro Gln
                170                 175                 180 ttc gaa aaa ggt ggc ggc ggt ggt aca cca gaa atg cct gtt ctg gaa     675
Phe Glu Lys Gly Gly Gly Gly Gly Thr Pro Glu Met Pro Val Leu Glu
                185                 190                 195 aac cgg gct gct cag ggc gat att act gca ccc ggc ggt gct cgc cgt     723
Asn Arg Ala Ala Gln Gly Asp Ile Thr Ala Pro Gly Gly Ala Arg Arg
            200                 205                 210 tta acg ggt gat cag act gcc gct ctg cgt gat tct ctt agc gat aaa     771
Leu Thr Gly Asp Gln Thr Ala Ala Leu Arg Asp Ser Leu Ser Asp Lys
        215                 220                 225 cct gca aaa aat att att ttg ctg att ggc gat ggg atg ggg gac tcg     819
Pro Ala Lys Asn Ile Ile Leu Leu Ile Gly Asp Gly Met Gly Asp Ser
230                 235                 240                 245 gaa att act gcc gca cgt aat tat gcc gaa ggt gcg ggc ggc ttt ttt     867
Glu Ile Thr Ala Ala Arg Asn Tyr Ala Glu Gly Ala Gly Gly Phe Phe
                250                 255                 260 aaa ggt ata gat gcc tta ccg ctt acc ggg caa tac act cac tat gcg     915
Lys Gly Ile Asp Ala Leu Pro Leu Thr Gly Gln Tyr Thr His Tyr Ala
                265                 270                 275 ctg aat aaa aaa acc ggc aaa ccg gac tac gtc acc gac tcg gct gca     963
Leu Asn Lys Lys Thr Gly Lys Pro Asp Tyr Val Thr Asp Ser Ala Ala
            280                 285                 290 tca gca acc gcc tgg tca acc ggt gtc aaa acc tat aac ggc gcg ctg    1011
Ser Ala Thr Ala Trp Ser Thr Gly Val Lys Thr Tyr Asn Gly Ala Leu
        295                 300                 305 ggc gtc gat att cac gaa aaa gat cac cca acg att ctg gaa atg gca    1059
Gly Val Asp Ile His Glu Lys Asp His Pro Thr Ile Leu Glu Met Ala
310                 315                 320                 325 aaa gcc gca ggt ctg gcg acc ggt aac gtt tct acc gca gag ttg cag    1107
Lys Ala Ala Gly Leu Ala Thr Gly Asn Val Ser Thr Ala Glu Leu Gln
                330                 335                 340 gat gcc acg ccc gct gcg ctg gtg gca cat gtg acc tcg cgc aaa tgc    1155
Asp Ala Thr Pro Ala Ala Leu Val Ala His Val Thr Ser Arg Lys Cys
                345                 350                 355 tac ggt ccg agc gcg acc agt gaa aaa tgt ccg ggt aac gct ctg gaa    1203
Tyr Gly Pro Ser Ala Thr Ser Glu Lys Cys Pro Gly Asn Ala Leu Glu
            360                 365                 370 aaa ggc gga aaa gga tcg att acc gaa cag ctg ctt aac gct cgt gcc    1251
```

```
Lys Gly Gly Lys Gly Ser Ile Thr Glu Gln Leu Leu Asn Ala Arg Ala
        375                 380                 385 gac gtt acg ctt ggc ggc ggc gca aaa acc ttt gct gaa acg gca acc      1299
Asp Val Thr Leu Gly Gly Gly Ala Lys Thr Phe Ala Glu Thr Ala Thr
390                 395                 400                 405 gct ggt gaa tgg cag gga aaa acg ctg cgt gaa cag gca cag gcg cgt      1347
Ala Gly Glu Trp Gln Gly Lys Thr Leu Arg Glu Gln Ala Gln Ala Arg
            410                 415                 420 ggt tat cag ttg gtg agc gat gct gcc tca ctg aat tcg gtg acg gaa      1395
Gly Tyr Gln Leu Val Ser Asp Ala Ala Ser Leu Asn Ser Val Thr Glu
        425                 430                 435 gcg aat cag caa aaa ccc ctg ctt ggc ctg ttt gct gac ggc aat atg      1443
Ala Asn Gln Gln Lys Pro Leu Leu Gly Leu Phe Ala Asp Gly Asn Met
    440                 445                 450 cca gtg cgc tgg cta gga ccg aaa gca acg tac cat ggc aat atc gat      1491
Pro Val Arg Trp Leu Gly Pro Lys Ala Thr Tyr His Gly Asn Ile Asp
455                 460                 465 aag ccc gca gtc acc tgt acg cca aat ccg caa cgt aat gac agt gta      1539
Lys Pro Ala Val Thr Cys Thr Pro Asn Pro Gln Arg Asn Asp Ser Val
470                 475                 480                 485 cca acc ctg gcg cag atg acc gac aaa gcc att gaa ttg ttg agt aaa      1587
Pro Thr Leu Ala Gln Met Thr Asp Lys Ala Ile Glu Leu Leu Ser Lys
                490                 495                 500 aat gag aaa ggc ttt ttc ctg caa gtt gaa ggt gcg tca atc gat aaa      1635
Asn Glu Lys Gly Phe Phe Leu Gln Val Glu Gly Ala Ser Ile Asp Lys
            505                 510                 515 cag gat cat gct gcg aat cct tgt ggg caa att ggc gag acg gtc gat      1683
Gln Asp His Ala Ala Asn Pro Cys Gly Gln Ile Gly Glu Thr Val Asp
        520                 525                 530 ctc gat gaa gcc gta caa cgg gcg ctg gaa ttc gct aaa aag gag ggt      1731
Leu Asp Glu Ala Val Gln Arg Ala Leu Glu Phe Ala Lys Lys Glu Gly
535                 540                 545 aac acg ctg gtc ata gtc acc gct gat cac gcc cac gcc agc cag att      1779
Asn Thr Leu Val Ile Val Thr Ala Asp His Ala His Ala Ser Gln Ile
550                 555                 560                 565 gtt gcg ccg gat acc aaa gct ccg ggc ctc acc cag gcg cta aat acc      1827
Val Ala Pro Asp Thr Lys Ala Pro Gly Leu Thr Gln Ala Leu Asn Thr
                570                 575                 580 aaa gat ggc gca gtg atg gtg atg agt tac ggg aac tcc gaa gag gat      1875
Lys Asp Gly Ala Val Met Val Met Ser Tyr Gly Asn Ser Glu Glu Asp
            585                 590                 595 tca caa gaa cat acc ggc agt cag ttg cgt att gcg gcg tat ggc ccg      1923
Ser Gln Glu His Thr Gly Ser Gln Leu Arg Ile Ala Ala Tyr Gly Pro
        600                 605                 610 cat gcc gcc aat gtt gtt gga ctg acc gac cag acc gat ctc ttc tac      1971
His Ala Ala Asn Val Val Gly Leu Thr Asp Gln Thr Asp Leu Phe Tyr
    615                 620                 625 acc atg aaa gcc gct ctg ggg ctg aaa taagctt                          2005
Thr Met Lys Ala Ala Leu Gly Leu Lys
630                 635

<210> SEQ ID NO 19
<211> LENGTH: 396
<212> TYPE: PRT
<213> ORGANISM: Artificial Sequence
<220> FEATURE:
<223> OTHER INFORMATION: Description of Artificial Sequence: Synthetic
      pBBP20 amino acid sequence

<400> SEQUENCE: 19

Met Lys Lys Thr Ala Ile Ala Ile Ala Val Ala Leu Ala Gly Phe Ala
```

-continued

```
                -20                 -15                 -10
Thr Val Ala Gln Ala Asp Val Tyr His Asp Gly Ala Cys Pro Glu Val
 -5              -1   1               5                  10

Lys Pro Val Asp Asn Phe Asp Trp Ser Gln Tyr His Gly Lys Trp Trp
             15                  20                  25

Glu Val Ala Lys Tyr Pro Asn Ser Val Glu Lys Tyr Gly Lys Cys Gly
         30                  35                  40

Trp Ala Glu Tyr Thr Pro Glu Gly Lys Ser Val Lys Val Ser Asn Tyr
     45                  50                  55

His Val Ile His Gly Lys Glu Tyr Phe Ile Glu Gly Thr Ala Tyr Pro
 60                  65                  70                  75

Val Gly Asp Ser Lys Ile Gly Lys Ile Tyr His Ser Leu Thr Tyr Gly
                 80                  85                  90

Gly Val Thr Lys Glu Asn Val Phe Asn Val Leu Ser Thr Asp Asn Lys
             95                 100                 105

Asn Tyr Ile Ile Gly Tyr Tyr Cys Lys Tyr Asp Glu Asp Lys Lys Gly
            110                 115                 120

His Gln Asp Phe Val Trp Val Leu Ser Arg Ser Met Val Leu Thr Gly
            125                 130                 135

Glu Ala Lys Thr Ala Val Glu Asn Tyr Leu Ile Gly Ser Pro Val Val
140                 145                 150                 155

Asp Ser Gln Lys Leu Val Tyr Ser Asp Phe Ser Glu Ala Ala Cys Lys
                160                 165                 170

Val Asn Asn Ser Asn Trp Ser His Pro Gln Phe Glu Lys Lys Ala Gly
            175                 180                 185

Gly Gly Ser Gly Gly Gly Ser Gly Gly Ser Glu Gly Gly Gly Ser
            190                 195                 200

Glu Gly Gly Gly Ser Glu Gly Gly Ser Glu Gly Gly Gly Ser Gly
205                 210                 215

Gly Gly Ser Gly Ser Gly Asp Phe Asp Tyr Glu Lys Met Ala Asn Ala
220                 225                 230                 235

Asn Lys Gly Ala Met Thr Glu Asn Ala Asp Glu Asn Ala Leu Gln Ser
            240                 245                 250

Asp Ala Lys Gly Lys Leu Asp Ser Val Ala Thr Asp Tyr Gly Ala Ala
            255                 260                 265

Ile Asp Gly Phe Ile Gly Asp Val Ser Gly Leu Ala Asn Gly Asn Gly
            270                 275                 280

Ala Thr Gly Asp Phe Ala Gly Ser Asn Ser Gln Met Ala Gln Val Gly
285                 290                 295

Asp Gly Asp Asn Ser Pro Leu Met Asn Asn Phe Arg Gln Tyr Leu Pro
300                 305                 310                 315

Ser Leu Pro Gln Ser Val Glu Cys Arg Pro Phe Val Phe Gly Ala Gly
                320                 325                 330

Lys Pro Tyr Glu Phe Ser Ile Asp Cys Asp Lys Ile Asn Leu Phe Arg
            335                 340                 345

Gly Val Phe Ala Phe Leu Leu Tyr Val Ala Thr Phe Met Tyr Val Phe
            350                 355                 360

Ser Thr Phe Ala Asn Ile Leu Arg Asn Lys Glu Ser
            365                 370                 375
```

<210> SEQ ID NO 20
<211> LENGTH: 254
<212> TYPE: PRT
<213> ORGANISM: Artificial Sequence

```
<220> FEATURE:
<223> OTHER INFORMATION: Description of Artificial Sequence: Fragment of
      synthetic pBBP22 amino acid sequence

<400> SEQUENCE: 20

Met Lys Lys Thr Ala Ile Ala Ile Ala Val Ala Leu Ala Gly Phe Ala
    -20                 -15                 -10
Thr Val Ala Gln Ala Asp Val Tyr His Asp Gly Ala Cys Pro Glu Val
 -5              -1   1               5                      10
Lys Pro Val Asp Asn Phe Asp Trp Ser Gln Tyr His Gly Lys Trp Trp
                 15                  20                  25
Glu Val Ala Lys Tyr Pro Asn Ser Val Glu Lys Tyr Gly Lys Cys Gly
             30                  35                  40
Trp Ala Glu Tyr Thr Pro Glu Gly Lys Ser Val Lys Val Ser Asn Tyr
 45                  50                  55
His Val Ile His Gly Lys Glu Tyr Phe Ile Glu Gly Thr Ala Tyr Pro
 60                  65                  70                  75
Val Gly Asp Ser Lys Ile Gly Lys Ile Tyr His Ser Leu Thr Tyr Gly
                 80                  85                  90
Gly Val Thr Lys Glu Asn Val Phe Asn Val Leu Ser Thr Asp Asn Lys
                 95                 100                 105
Asn Tyr Ile Ile Gly Tyr Tyr Cys Lys Tyr Asp Glu Asp Lys Lys Gly
                110                 115                 120
His Gln Asp Phe Val Trp Val Leu Ser Arg Ser Met Val Leu Thr Gly
                125                 130                 135
Glu Ala Lys Thr Ala Val Glu Asn Tyr Leu Ile Gly Ser Pro Val Val
140                 145                 150                 155
Asp Ser Gln Lys Leu Val Tyr Ser Asp Phe Ser Glu Ala Ala Cys Lys
                160                 165                 170
Val Asn Asn Ser Asn Trp Ser His Pro Gln Phe Glu Lys Pro Ala Ser
                175                 180                 185
Leu Ala Glu Ala Lys Val Leu Ala Asn Arg Glu Leu Asp Lys Tyr Gly
                190                 195                 200
Val Ser Asp Tyr Tyr Lys Asn Leu Ile Asn Asn Ala Lys Thr Val Glu
205                 210                 215
Gly Val Lys Ala Leu Ile Asp Glu Ile Leu Ala Ala Leu Pro
220                 225                 230

<210> SEQ ID NO 21
<211> LENGTH: 174
<212> TYPE: PRT
<213> ORGANISM: Artificial Sequence
<220> FEATURE:
<223> OTHER INFORMATION: Description of Artificial Sequence: Synthetic
      DigA amino acid sequence

<400> SEQUENCE: 21

Asp Val Tyr His Asp Gly Ala Cys Pro Glu Val Lys Pro Val Asp Asn
  1               5                  10                  15
Phe Asp Trp Ser Gln Tyr His Gly Lys Trp Trp Glu Val Ala Lys Tyr
                 20                  25                  30
Pro His His Glu Arg Lys Tyr Gly Lys Cys Gly Trp Ala Glu Tyr Thr
                 35                  40                  45
Pro Glu Gly Lys Ser Val Lys Val Ser Arg Tyr Ser Val Ile His Gly
 50                  55                  60
Lys Glu Tyr Phe Ser Glu Gly Thr Ala Tyr Pro Val Gly Asp Ser Lys
 65                  70                  75                  80
```

```
Ile Gly Lys Ile Tyr His Ser Tyr Thr Ile Gly Gly Val Thr Gln Glu
                85                  90                  95

Gly Val Phe Asn Val Leu Ser Thr Asp Asn Lys Asn Tyr Ile Ile Gly
            100                 105                 110

Tyr Phe Cys Ser Tyr Asp Glu Asp Lys Lys Gly His Met Asp Leu Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170
```

<210> SEQ ID NO 22
<211> LENGTH: 394
<212> TYPE: PRT
<213> ORGANISM: Artificial Sequence
<220> FEATURE:
<223> OTHER INFORMATION: Description of Artificial Sequence: Fragment of
      synthetic pBBP24 amino acid sequence

<400> SEQUENCE: 22

```
Met Lys Lys Thr Ala Ile Ala Ile Ala Val Ala Leu Ala Gly Phe Ala
    -20                 -15                 -10

Thr Val Ala Gln Ala Asp Val Tyr His Asp Gly Ala Cys Pro Glu Val
 -5              -1   1               5                  10

Lys Pro Val Asp Asn Phe Asp Trp Ser Gln Tyr His Gly Lys Trp Trp
                15                  20                  25

Glu Val Ala Lys Tyr Pro Asn Ser Val Glu Lys Tyr Gly Asn Trp Ala
            30                  35                  40

Glu Tyr Thr Pro Glu Gly Lys Ser Val Lys Val Ser Asn Tyr His Val
        45                  50                  55

Ile His Gly Lys Glu Tyr Phe Ile Glu Gly Thr Ala Tyr Pro Val Gly
60                  65                  70                  75

Asp Ser Lys Ile Gly Lys Ile Tyr His Ser Leu Thr Tyr Gly Gly Val
                80                  85                  90

Thr Lys Glu Asn Val Phe Asn Val Leu Ser Thr Asp Asn Lys Asn Tyr
            95                  100                 105

Ile Ile Gly Tyr Tyr Cys Lys Tyr Asp Glu Asp Lys Lys Gly His Gln
        110                 115                 120

Asp Phe Val Trp Val Leu Ser Arg Ser Met Val Leu Thr Gly Glu Ala
    125                 130                 135

Lys Thr Ala Val Glu Asn Tyr Leu Ile Gly Ser Pro Val Val Asp Ser
140                 145                 150                 155

Gln Lys Leu Val Tyr Ser Asp Phe Ser Glu Ala Ala Cys Lys Val Asn
                160                 165                 170

Asn Ser Asn Trp Ser His Pro Gln Phe Glu Lys Lys Ala Gly Gly Gly
            175                 180                 185

Ser Gly Gly Gly Ser Gly Gly Ser Glu Gly Gly Ser Glu Gly
        190                 195                 200

Gly Gly Ser Glu Gly Gly Ser Gly Gly Ser Gly Gly
    205                 210                 215

Ser Gly Ser Gly Asp Phe Asp Tyr Glu Lys Met Ala Asn Ala Asn Lys
220                 225                 230                 235

Gly Ala Met Thr Glu Asn Ala Asp Glu Asn Ala Leu Gln Ser Asp Ala
```

```
                240                 245                 250
Lys Gly Lys Leu Asp Ser Val Ala Thr Asp Tyr Gly Ala Ala Ile Asp
                    255                 260                 265

Gly Phe Ile Gly Asp Val Ser Gly Leu Ala Asn Gly Asn Gly Ala Thr
                270                 275                 280

Gly Asp Phe Ala Gly Ser Asn Ser Gln Met Ala Gln Val Gly Asp Gly
            285                 290                 295

Asp Asn Ser Pro Leu Met Asn Asn Phe Arg Gln Tyr Leu Pro Ser Leu
300                 305                 310                 315

Pro Gln Ser Val Glu Cys Arg Pro Phe Val Phe Gly Ala Gly Lys Pro
                    320                 325                 330

Tyr Glu Phe Ser Ile Asp Cys Asp Lys Ile Asn Leu Phe Arg Gly Val
                335                 340                 345

Phe Ala Phe Leu Leu Tyr Val Ala Thr Phe Met Tyr Val Phe Ser Thr
            350                 355                 360

Phe Ala Asn Ile Leu Arg Asn Lys Glu Ser
        365                 370

<210> SEQ ID NO 23
<211> LENGTH: 174
<212> TYPE: PRT
<213> ORGANISM: Artificial Sequence
<220> FEATURE:
<223> OTHER INFORMATION: Description of Artificial Sequence: Mutein
      DigA16 amino acid sequence

<400> SEQUENCE: 23

Asp Val Tyr His Asp Gly Ala Cys Pro Glu Val Lys Pro Val Asp Asn
  1               5                  10                  15

Phe Asp Trp Ser Gln Tyr His Gly Lys Trp Trp Gln Val Ala Ala Tyr
                 20                  25                  30

Pro Asp His Ile Thr Lys Tyr Gly Lys Cys Gly Trp Ala Glu Tyr Thr
             35                  40                  45

Pro Glu Gly Lys Ser Val Lys Val Ser Arg Tyr Ser Val Ile His Gly
     50                  55                  60

Lys Glu Tyr Phe Ser Glu Gly Thr Ala Tyr Pro Val Gly Asp Ser Lys
 65                  70                  75                  80

Ile Gly Lys Ile Tyr His Ser Tyr Thr Ile Gly Gly Val Thr Gln Glu
                 85                  90                  95

Gly Val Phe Asn Val Leu Ser Thr Asp Asn Lys Asn Tyr Ile Ile Gly
            100                 105                 110

Tyr Phe Cys Ser Tyr Asp Glu Asp Lys Lys Gly His Met Asp Leu Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 24
<211> LENGTH: 205
<212> TYPE: PRT
<213> ORGANISM: Artificial Sequence
<220> FEATURE:
<223> OTHER INFORMATION: Description of Artificial Sequence: Fragment of
      synthetic pBBP21 amino acid sequence
```

```
<400> SEQUENCE: 24

Met Lys Lys Thr Ala Ile Ala Ile Ala Val Ala Leu Ala Gly Phe Ala
    -20             -15             -10

Thr Val Ala Gln Ala Asp Val Tyr His Asp Gly Ala Cys Pro Glu Val
 -5              -1   1               5                      10

Lys Pro Val Asp Asn Phe Asp Trp Ser Gln Tyr His Gly Lys Trp Trp
             15              20              25

Glu Val Ala Lys Tyr Pro Asn Ser Val Glu Lys Tyr Gly Lys Cys Gly
             30              35              40

Trp Ala Glu Tyr Thr Pro Glu Gly Lys Ser Val Lys Val Ser Asn Tyr
 45              50              55

His Val Ile His Gly Lys Glu Tyr Phe Ile Glu Gly Thr Ala Tyr Pro
 60              65              70              75

Val Gly Asp Ser Lys Ile Gly Lys Ile Tyr His Ser Leu Thr Tyr Gly
                 80              85              90

Gly Val Thr Lys Glu Asn Val Phe Asn Val Leu Ser Thr Asp Asn Lys
             95              100             105

Asn Tyr Ile Ile Gly Tyr Tyr Cys Lys Tyr Asp Glu Asp Lys Lys Gly
         110             115             120

His Gln Asp Phe Val Trp Val Leu Ser Arg Ser Met Val Leu Thr Gly
 125             130             135

Glu Ala Lys Thr Ala Val Glu Asn Tyr Leu Ile Gly Ser Pro Val Val
 140             145             150             155

Asp Ser Gln Lys Leu Val Tyr Ser Asp Phe Ser Glu Ala Ala Cys Lys
             160             165             170

Val Asn Asn Ser Asn Trp Ser His Pro Gln Phe Glu Lys
             175             180

<210> SEQ ID NO 25
<211> LENGTH: 236
<212> TYPE: PRT
<213> ORGANISM: Artificial Sequence
<220> FEATURE:
<223> OTHER INFORMATION: Description of Artificial Sequence: Fragment of
      synthetic pBBP21 amino acid sequence

<400> SEQUENCE: 25

Met Lys Lys Gly Phe Met Leu Phe Thr Leu Leu Ala Ala Phe Ser Gly
    -20             -15             -10              -5

Phe Ala Gln Ala Asp Asp Ala Ala Ile Gln Gln Thr Leu Ala Lys Met
             -1   1               5              10

Gly Ile Lys Ser Ser Asp Ile Gln Pro Ala Pro Val Ala Gly Met Lys
             15              20              25

Thr Val Leu Thr Asn Ser Gly Val Leu Tyr Ile Thr Asp Asp Gly Lys
         30              35              40

His Ile Ile Gln Gly Pro Met Tyr Asp Val Ser Gly Thr Ala Pro Val
 45              50              55              60

Asn Val Thr Asn Lys Met Leu Leu Lys Gln Leu Asn Ala Leu Glu Lys
             65              70              75

Glu Met Ile Val Tyr Lys Ala Pro Gln Glu Lys His Val Ile Thr Val
             80              85              90

Phe Thr Asp Ile Thr Cys Gly Tyr Cys His Lys Leu His Glu Gln Met
         95              100             105

Ala Asp Tyr Asn Ala Leu Gly Ile Thr Val Arg Tyr Leu Ala Phe Pro
 110             115             120
```

Arg Gln Gly Leu Asp Ser Asp Ala Glu Lys Glu Met Lys Ala Ile Trp
125                 130                 135                 140

Cys Ala Lys Asp Lys Asn Lys Ala Phe Asp Asp Val Met Ala Gly Lys
            145                 150                 155

Ser Val Ala Pro Ala Ser Cys Asp Val Asp Ile Ala Asp His Tyr Ala
            160                 165                 170

Leu Gly Val Gln Leu Gly Val Ser Gly Thr Pro Ala Val Val Leu Ser
        175                 180                 185

Asn Gly Thr Leu Val Pro Gly Tyr Gln Pro Pro Lys Glu Met Lys Glu
    190                 195                 200

Phe Leu Asp Glu His Gln Lys Met Thr Ser Gly Lys
205                 210                 215

<210> SEQ ID NO 26
<211> LENGTH: 659
<212> TYPE: PRT
<213> ORGANISM: Artificial Sequence
<220> FEATURE:
<223> OTHER INFORMATION: Description of Artificial Sequence: Fragment of
      synthetic pBBP27 amino acid sequence

<400> SEQUENCE: 26

Val Lys Gln Ser Thr Ile Ala Leu Ala Leu Leu Pro Leu Leu Phe Thr
    -20                 -15                 -10

Pro Val Thr Lys Ala Arg Thr Pro Glu Met Pro Val Leu Glu Asn Arg
    -5              -1   1               5                   10

Ala Ala Gln Gly Asp Ile Thr Ala Pro Gly Gly Ala Arg Arg Leu Thr
            15                  20                  25

Gly Asp Gln Thr Ala Ala Leu Arg Asp Ser Leu Ser Asp Lys Pro Ala
        30                  35                  40

Lys Asn Ile Ile Leu Leu Ile Gly Asp Gly Met Gly Asp Ser Glu Ile
    45                  50                  55

Thr Ala Ala Arg Asn Tyr Ala Glu Gly Ala Gly Gly Phe Phe Lys Gly
60                  65                  70                  75

Ile Asp Ala Leu Pro Leu Thr Gly Gln Tyr Thr His Tyr Ala Leu Asn
            80                  85                  90

Lys Lys Thr Gly Lys Pro Asp Tyr Val Thr Asp Ser Ala Ala Ser Ala
        95                  100                 105

Thr Ala Trp Ser Thr Gly Val Lys Thr Tyr Asn Gly Ala Leu Gly Val
        110                 115                 120

Asp Ile His Glu Lys Asp His Pro Thr Ile Leu Glu Met Ala Lys Ala
    125                 130                 135

Ala Gly Leu Ala Thr Gly Asn Val Ser Thr Ala Glu Leu Gln Asp Ala
140                 145                 150                 155

Thr Pro Ala Ala Leu Val Ala His Val Thr Ser Arg Lys Cys Tyr Gly
            160                 165                 170

Pro Ser Ala Thr Ser Glu Lys Cys Pro Gly Asn Ala Leu Glu Lys Gly
        175                 180                 185

Gly Lys Gly Ser Ile Thr Glu Gln Leu Leu Asn Ala Arg Ala Asp Val
        190                 195                 200

Thr Leu Gly Gly Gly Ala Lys Thr Phe Ala Glu Thr Ala Thr Ala Gly
    205                 210                 215

Glu Trp Gln Gly Lys Thr Leu Arg Glu Gln Ala Gln Ala Arg Gly Tyr
220                 225                 230                 235

Gln Leu Val Ser Asp Ala Ala Ser Leu Asn Ser Val Thr Glu Ala Asn
            240                 245                 250

```
Gln Gln Lys Pro Leu Leu Gly Leu Phe Ala Asp Gly Asn Met Pro Val
            255                 260                 265
Arg Trp Leu Gly Pro Lys Ala Thr Tyr His Gly Asn Ile Asp Lys Pro
            270                 275                 280
Ala Val Thr Cys Thr Pro Asn Pro Gln Arg Asn Asp Ser Val Pro Thr
            285                 290                 295
Leu Ala Gln Met Thr Asp Lys Ala Ile Glu Leu Leu Ser Lys Asn Glu
300                 305                 310                 315
Lys Gly Phe Phe Leu Gln Val Glu Gly Ala Ser Ile Asp Lys Gln Asp
                320                 325                 330
His Ala Ala Asn Pro Cys Gly Gln Ile Gly Glu Thr Val Asp Leu Asp
                335                 340                 345
Glu Ala Val Gln Arg Ala Leu Glu Phe Ala Lys Lys Glu Gly Asn Thr
                350                 355                 360
Leu Val Ile Val Thr Ala Asp His Ala His Ala Ser Gln Ile Val Ala
            365                 370                 375
Pro Asp Thr Lys Ala Pro Gly Leu Thr Gln Ala Leu Asn Thr Lys Asp
380                 385                 390                 395
Gly Ala Val Met Val Met Ser Tyr Gly Asn Ser Glu Glu Asp Ser Gln
                400                 405                 410
Glu His Thr Gly Ser Gln Leu Arg Ile Ala Ala Tyr Gly Pro His Ala
                415                 420                 425
Ala Asn Val Val Gly Leu Thr Asp Gln Thr Asp Leu Phe Tyr Thr Met
            430                 435                 440
Lys Ala Ala Leu Gly Leu Lys Pro Pro Ser Ala Asp Val Tyr His Asp
            445                 450                 455
Gly Ala Cys Pro Glu Val Lys Pro Val Asp Asn Phe Asp Trp Ser Gln
460                 465                 470                 475
Tyr His Gly Lys Trp Trp Gln Val Ala Ala Tyr Pro Asp His Ile Thr
                480                 485                 490
Lys Tyr Gly Lys Cys Gly Trp Ala Glu Tyr Thr Pro Glu Gly Lys Ser
            495                 500                 505
Val Lys Val Ser Arg Tyr Ser Val Ile His Gly Lys Glu Tyr Phe Ser
510                 515                 520
Glu Gly Thr Ala Tyr Pro Val Gly Asp Ser Lys Ile Gly Lys Ile Tyr
            525                 530                 535
His Ser Tyr Thr Ile Gly Gly Val Thr Gln Glu Gly Val Phe Asn Val
540                 545                 550                 555
Leu Ser Thr Asp Asn Lys Asn Tyr Ile Ile Gly Tyr Phe Cys Ser Tyr
                560                 565                 570
Asp Glu Asp Lys Lys Gly His Met Asp Leu Val Trp Val Leu Ser Arg
            575                 580                 585
Ser Met Val Leu Thr Gly Glu Ala Lys Thr Ala Val Glu Asn Tyr Leu
            590                 595                 600
Ile Gly Ser Pro Val Val Asp Ser Gln Lys Leu Val Tyr Ser Asp Phe
            605                 610                 615
Ser Glu Ala Ala Cys Lys Val Asn Asn Ser Asn Trp Ser His Pro Gln
620                 625                 630                 635
Phe Glu Lys

<210> SEQ ID NO 27
<211> LENGTH: 659
<212> TYPE: PRT
```

<213> ORGANISM: Artificial Sequence
<220> FEATURE:
<223> OTHER INFORMATION: Description of Artificial Sequence: Fragment of synthetic pBBP29 amino acid sequence

<400> SEQUENCE: 27

```
Met Lys Lys Thr Ala Ile Ala Ile Ala Val Ala Leu Ala Gly Phe Ala
    -20             -15                 -10

Thr Val Ala Gln Ala Asp Val Tyr His Asp Gly Ala Cys Pro Glu Val
 -5              -1   1               5                      10

Lys Pro Val Asp Asn Phe Asp Trp Ser Gln Tyr His Gly Lys Trp Trp
             15                  20                  25

Gln Val Ala Ala Tyr Pro Asp His Ile Thr Lys Tyr Gly Lys Cys Gly
             30                  35                  40

Trp Ala Glu Tyr Thr Pro Glu Gly Lys Ser Val Lys Val Ser Arg Tyr
     45                  50                  55

Ser Val Ile His Gly Lys Glu Tyr Phe Ser Glu Gly Thr Ala Tyr Pro
 60              65                  70                      75

Val Gly Asp Ser Lys Ile Gly Lys Ile Tyr His Ser Tyr Thr Ile Gly
                 80                  85                  90

Gly Val Thr Gln Glu Gly Val Phe Asn Val Leu Ser Thr Asp Asn Lys
                 95                 100                 105

Asn Tyr Ile Ile Gly Tyr Phe Cys Ser Tyr Asp Glu Asp Lys Lys Gly
                110                 115                 120

His Met Asp Leu Val Trp Val Leu Ser Arg Ser Met Val Leu Thr Gly
    125                 130                 135

Glu Ala Lys Thr Ala Val Glu Asn Tyr Leu Ile Gly Ser Pro Val Val
140             145                 150                 155

Asp Ser Gln Lys Leu Val Tyr Ser Asp Phe Ser Glu Ala Ala Cys Lys
                160                 165                 170

Val Asn Asn Ser Asn Trp Ser His Pro Gln Phe Glu Lys Gly Gly Gly
                175                 180                 185

Gly Gly Thr Pro Glu Met Pro Val Leu Glu Asn Arg Ala Ala Gln Gly
        190                 195                 200

Asp Ile Thr Ala Pro Gly Gly Ala Arg Arg Leu Thr Gly Asp Gln Thr
    205                 210                 215

Ala Ala Leu Arg Asp Ser Leu Ser Asp Lys Pro Ala Lys Asn Ile Ile
220                 225                 230                 235

Leu Leu Ile Gly Asp Gly Met Gly Asp Ser Glu Ile Thr Ala Ala Arg
                240                 245                 250

Asn Tyr Ala Glu Gly Ala Gly Gly Phe Phe Lys Gly Ile Asp Ala Leu
                255                 260                 265

Pro Leu Thr Gly Gln Tyr Thr His Tyr Ala Leu Asn Lys Lys Thr Gly
                270                 275                 280

Lys Pro Asp Tyr Val Thr Asp Ser Ala Ser Ala Thr Ala Trp Ser
                285                 290                 295

Thr Gly Val Lys Thr Tyr Asn Gly Ala Leu Gly Val Asp Ile His Glu
300                 305                 310                 315

Lys Asp His Pro Thr Ile Leu Glu Met Ala Lys Ala Ala Gly Leu Ala
                320                 325                 330

Thr Gly Asn Val Ser Thr Ala Glu Leu Gln Asp Ala Thr Pro Ala Ala
                335                 340                 345

Leu Val Ala His Val Thr Ser Arg Lys Cys Tyr Gly Pro Ser Ala Thr
                350                 355                 360
```

```
Ser Glu Lys Cys Pro Gly Asn Ala Leu Glu Lys Gly Gly Lys Gly Ser
365                 370                 375

Ile Thr Glu Gln Leu Leu Asn Ala Arg Ala Asp Val Thr Leu Gly Gly
380                 385                 390                 395

Gly Ala Lys Thr Phe Ala Glu Thr Ala Thr Ala Gly Glu Trp Gln Gly
                400                 405                 410

Lys Thr Leu Arg Glu Gln Ala Gln Ala Arg Gly Tyr Gln Leu Val Ser
            415                 420                 425

Asp Ala Ala Ser Leu Asn Ser Val Thr Glu Ala Asn Gln Gln Lys Pro
            430                 435                 440

Leu Leu Gly Leu Phe Ala Asp Gly Asn Met Pro Val Arg Trp Leu Gly
445                 450                 455

Pro Lys Ala Thr Tyr His Gly Asn Ile Asp Lys Pro Ala Val Thr Cys
460                 465                 470                 475

Thr Pro Asn Pro Gln Arg Asn Asp Ser Val Pro Thr Leu Ala Gln Met
                480                 485                 490

Thr Asp Lys Ala Ile Glu Leu Leu Ser Lys Asn Glu Lys Gly Phe Phe
            495                 500                 505

Leu Gln Val Glu Gly Ala Ser Ile Asp Lys Gln Asp His Ala Ala Asn
510                 515                 520

Pro Cys Gly Gln Ile Gly Glu Thr Val Asp Leu Asp Glu Ala Val Gln
525                 530                 535

Arg Ala Leu Glu Phe Ala Lys Lys Glu Gly Asn Thr Leu Val Ile Val
540                 545                 550                 555

Thr Ala Asp His Ala His Ala Ser Gln Ile Val Ala Pro Asp Thr Lys
                560                 565                 570

Ala Pro Gly Leu Thr Gln Ala Leu Asn Thr Lys Asp Gly Ala Val Met
            575                 580                 585

Val Met Ser Tyr Gly Asn Ser Glu Glu Asp Ser Gln Glu His Thr Gly
            590                 595                 600

Ser Gln Leu Arg Ile Ala Ala Tyr Gly Pro His Ala Ala Asn Val Val
            605                 610                 615

Gly Leu Thr Asp Gln Thr Asp Leu Phe Tyr Thr Met Lys Ala Ala Leu
620                 625                 630                 635

Gly Leu Lys

<210> SEQ ID NO 28
<211> LENGTH: 174
<212> TYPE: PRT
<213> ORGANISM: Pieris brassicae

<400> SEQUENCE: 28

Asp Val Tyr His Asp Gly Ala Cys Pro Glu Val Lys Pro Val Asp Asn
1               5                   10                  15

Phe Asp Trp Ser Gln Tyr His Gly Lys Trp Trp Glu Val Ala Lys Tyr
                20                  25                  30

Pro Asn Ser Val Glu Lys Tyr Gly Lys Cys Gly Trp Ala Glu Tyr Thr
            35                  40                  45

Pro Glu Gly Lys Ser Val Lys Val Ser Asn Tyr His Val Ile His Gly
        50                  55                  60

Lys Glu Tyr Phe Ile Glu Gly Thr Ala Tyr Pro Val Gly Asp Ser Lys
65                  70                  75                  80

Ile Gly Lys Ile Tyr His Ser Leu Thr Tyr Gly Gly Val Thr Lys Glu
                85                  90                  95
```

```
Asn Val Phe Asn Val Leu Ser Thr Asp Asn Lys Asn Tyr Ile Ile Gly
            100                 105                 110

Tyr Tyr Cys Lys Tyr Asp Glu Asp Lys Lys Gly His Gln Asp Phe Val
        115                 120                 125

Trp Val Leu Ser Arg Ser Met Val Leu Thr Gly Glu Ala Lys Thr Ala
    130                 135                 140

Val Glu Asn Tyr Leu Ile Gly Ser Pro Val Val Asp Ser Gln Lys Leu
145                 150                 155                 160

Val Tyr Ser Asp Phe Ser Glu Ala Ala Cys Lys Val Asn Asn
                165                 170

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 29

Pro Pro Ser Ala
  1
```

MUTEINS OF BILIN-BINDING PROTEIN

This application is a national stage entry under 35 U.S.C. § 371 of PCT patent application no. PCT/DE00/01873 filed on Jun. 8, 2000, which claims priority to German patent application no. 19926068, filed on Jun. 8, 1999.

The present invention relates to muteins of the bilin-binding protein which are capable of binding digoxigenin and to fusion proteins of such muteins, to methods for preparing muteins of this kind and their fusion proteins and also to the use thereof for detecting or binding biomolecules labeled with digoxigenin.

In molecular biology, the digoxigenin group is these days a very common instrument for nonradioactive detection of nucleic acids, proteins and other biomolecules. For this purpose, the biomolecule is, mostly covalently, modified with a reactive digoxigenin derivative, thus allowing subsequent detection of the molecule using an antibody directed against the digoxigenin group or a conjugate of an appropriate antibody fragment and a reporter enzyme, according to generally used methods in biochemistry.

The skilled worker knows quite a number of reactive digoxigenin derivatives, which are in part also commercially available. For example, digoxigenin-3-O-methylcarbonyl-ϵ-aminocaproic acid N-hydroxysuccinimide ester (DIG-NHS), digoxigenin-3-O-succinyl-ϵ-amino-caproic acid N-hydroxysuccinimide ester and 3-amino-3-deoxydigoxigenin-hemisuccinimide succinimidyl ester are suitable for covalent coupling to proteins, in particular to the amino groups of exposed lysine side chains. Using 3-iodoacetylamino-3-deoxydigoxigenin it is possible to label especially thiol groups in proteins or in other biomolecules in a selective manner with the digoxigenin group. It is possible to couple synthetic oligodeoxynucleotides to the same reactive digoxigenin derivatives, as long as they have been equipped with suitable free amino or thiol groups during synthesis.

In addition, cis-platinum complexes of digoxigenin derivatives (DIG Chem-Link reagent) or digoxigenin derivatives containing carbodiimide groups (disclosed in the European patent specification EP 0 806 431 A2) are suitable for the direct labeling of nucleic acids. Alternatively, it is possible in the case of deoxyribonucleic acids to label said deoxyribonucleic acids during a template-dependent enzymatic synthesis with the aid of a DNA polymerase and a deoxynucleotide triphosphate coupled to the digoxigenin group, for example digoxigenin-11-dUTP, digoxigenin-11-ddUTP or digoxigenin-16-dATP. Analogously, digoxigenin-11-UTP is suitable for incorporation into enzymatically synthesized RNA. Moreover, it is possible to label oligodeoxynucleotides with the digoxigenin group directly in the automated DNA synthesis by using suitable activated building blocks, for example so-called "virtual nucleotides". Digoxigenin group-coupled nucleic acids of this kind are suitable as nonradioactive gene probes for detection of complementary nucleotide sequences by hybridization, for example in Northern or Southern blots (disclosed in the European patent specification EP 0 324 474 A1).

Digoxigenin group-labeled proteins or glycoproteins are particularly useful for determining, for example, relevant antigens or antibodies directed there against in immunochemical assay methods such as ELISA (enzyme-linked immunosorbent assay). The biomolecule conjugated with the digoxigenin group is actually detected using an anti-digoxigenin antibody, normally in the form of a conjugate of the Fab fragment of said antibody with a suitable enzyme, such as, for example, alkaline phosphatase or horseradish peroxidase, as label. The enzymatic activity then serves for quantification via catalysis of a chromogenic, fluorogenic or chemiluminescent reaction. Various antibodies against the digoxigenin group are known (Mudgett-Hunter et al., J. Immunol. 129 (1982), 1165–1172; Jeffrey et al., J. Mol. Biol. 248 (1995), 344–360).

The use of antibodies, however, has several disadvantages. Hence, the preparation of monoclonal antibodies in hybridoma cell cultures is complicated, and the proteolysis for the Fab fragment and also the production of conjugates with reporter enzymes requires additional difficult processing steps. But even the production of antibodies by genetic engineering is not simple, and the main reason for this is that antibodies as well as their antigen-binding fragments are composed of two different polypeptide chains in a structurally complicated manner. For the genetic manipulation of antibodies it is therefore necessary to handle two genes simultaneously. Moreover, the yield of correctly folded antibody fragments produced by genetic engineering is often low. As is known to the skilled worker, this is even more so when recombinant fusion proteins are to be prepared from Fab fragments of antibodies and enzymes.

It was therefore the object of the invention to develop alternative polypeptide reagents for detection of the digoxigenin group, which can be produced in a simple manner.

In an evolutionary research approach, it has surprisingly been found now that muteins of the bilin-binding protein, which is structurally based on a single polypeptide chain (Schmidt and Skerra, Eur. J. Biochem. 219 (1994), 855–863), are suitable for detecting the digoxigenin group by binding with high affinity, whereby the recognition of digoxigenin is astoundingly selective compared with other steroids.

The present invention thus relates to a polypeptide, selected from muteins of the bilin-binding protein, which is characterized in that it
(a) is able to bind digoxigenin or digoxigenin conjugates,
(b) does not bind ouabain, testosterone, and 4-aminofluorescein and
(c) has an amino acid substitution at at least one of the sequence positions 28, 31, 34, 35, 36, 37, 58, 60, 69, 88, 90, 95, 97, 114, 116, 125, and 127 of the bilin-binding protein.

In this connection, preference is given to digoxigenin-binding muteins which have an amino acid substitution at at least 4 to 7 or, preferably, at least 8 to 12 of the sequence positions defined above. A particularly preferred mutein is the polypeptide which has the amino acid sequence encoded by SEQ ID NO. 15.

Outside the region of the amino acid positions 28, 31, 34, 35, 36, 37, 58, 60, 69, 88, 90, 95, 97, 114, 116, 125, and 127 the muteins of the present invention may correspond to the amino acid sequence of the bilin-binding protein from *Pieris brassicae*. On the other hand, the amino acid sequence of the polypeptides of the invention may also have differences to the bilin-binding protein apart from said positions. Bilin-binding protein sequence variants of this kind comprise naturally occurring and also artificially generated variants, and the deviations mean substitutions, insertions, deletions of amino acid residues and also N- and/or C-terminal additions.

For example, the inventive muteins of the bilin-binding protein may have amino acid substitutions which prevent oligomerization of the bilin-binding protein, such as the Asn(1)->Asp substitution, or suppress proteolytic cleavage within the polypeptide chain, which may occur during production in *E. coli*, such as, for example, by the Lys(87)-

>Ser substitution. Furthermore, the mutations Asn(21)->Gln and Lys(135)->Met may be introduced into the nucleic acid coding for the muteins of the bilin-binding protein, in order to facilitate, for example, cloning of a gene segment via two new BstXI restriction cleavage sites at these positions. Likewise, the present invention relates to the specific introduction of amino acid substitutions within or outside the said positions, in order to generally improve particular properties of the mutein of the invention, for example its folding stability or folding efficiency or its resistance to proteases.

The ability of the polypeptides of the invention to bind digoxigenin or digoxigenin conjugates can be determined by common methods, for example ELISA, fluorescence titration, titration calorimetry, surface plasmon resonance measurements or blotting methods, for example Western blotting, Southern blotting or Northern blotting. Blotting methods may be used in order to transfer conjugates of digoxigenin with proteins or nucleic acids to a membrane and then detect said conjugates using one of the muteins of the invention, a conjugate of this mutein or a fusion protein of this mutein.

A quantitative parameter for binding affinity is provided by established thermodynamic parameters such as, for example, the affinity constant or dissociation constant for the complex of mutein and bound ligand, for example digoxigenin. However, it is also possible to determine the binding ability qualitatively, for example based on the intensity of a binding signal due to a chromogenic reaction or of a colored precipitate which is obtained with the aid of one of said blotting methods.

Preferred muteins of the invention are obtainable in a two-stage evolutionary process. Random mutagenesis of the bilin-binding protein at at least one, preferably at least 4 to 7, and particularly preferably at least 8 to 12, of the sequence positions 28, 31, 34, 35, 36, 37, 58, 60, 69, 88, 90, 95, 97, 114, 116, 125, and 127 and subsequent simple or, preferably, repeated selection of muteins with affinity for the digoxigenin group from this library, preferably using free digoxigenin or digitoxigenin for competitive enrichment, provides muteins of the bilin-binding protein which recognize the digoxigenin group, but the affinity is still comparatively low. Renewed mutagenesis of such a mutein at at least one, preferably at least 3 or 4, or at all of amino acid positions 28, 31, 34, 35, 36 and 37, now followed by a simple or, preferably, repeated enrichment by formation of a complex with the digoxigenin group and by subsequent dissociation of the formed complex in an acidic or basic milieu, then results in obtaining muteins having substantially higher affinity for the digoxigenin group. The digoxigenin group is preferably present as a digoxigenin/biotin double conjugate during said enrichment.

Surprisingly, it has now been found that the affinity constant between such polypeptides of the invention and digoxigenin is at least $10^7$ $M^{-1}$. This means in other words that the dissociation constant of the complex between the polypeptide of the invention and digoxigenin is 100 nM or less. Individual species even show dissociation constants of 35 nM or less, as illustrated in the Examples.

Besides digoxigenin, the inventive muteins of the bilin-binding protein can also bind digoxigenin derivatives as ligands, for example digoxin, digitoxin or digitoxigenin. Furthermore, the inventive muteins of the bilin-binding protein may bind conjugates of said chemical compounds, i.e. nucleic acids, polypeptides, carbohydrates, other natural or synthetic biomolecules, macromolecules or low molecular weight compounds which are covalently linked or linked via a metal complex to digoxigenin, digoxin, digitoxin or digitoxigenin. Preference is given to using for the preparation of such conjugates the reactive derivatives of digoxigenin, digoxin, digitoxin or digitoxigenin, which are known to the skilled worker and are stated, for example, further above.

Preferred muteins of the invention, which were obtained by the two-stage process described, show, compared with the affinity for digoxigenin, an even higher affinity for digitoxin or digitoxigenin, whose steroid system differs from that of digoxigenin only by the absence of a hydroxyl group. Surprisingly, these muteins show distinctive specificity with respect to the digoxigenin or digitoxigenin group, and this is shown by the fact that other steroids or steroid groups such as ouabain or testosterone are bound with much less affinity, if at all. Fluorescein derivatives such as 4-amino-fluorescein, too, are evidently not bound. This means that ouabain, testosterone or 4-aminofluorescein in each case exhibit a dissociation constant of at least 10 $\mu$M, preferably at least 100 $\mu$M, with respect to the inventive muteins of the bilin-binding protein.

This property of specificity distinguishes said muteins considerably from other muteins of the bilin-binding protein and also from antibodies directed against the digoxigenin group, such as, for example, the antibody 26-10 (Chen et al., Protein Eng. 12 (1999), 349–356), which binds ouabain with substantial affinity, and gives the inventive muteins of the bilin-binding protein a particular advantage. It is surprising that particularly the additional amino acid substitutions at positions 28, 31, 34, 35, 36, and 37 lead to the preferred muteins of the bilin-binding protein. Preference is therefore given to those muteins which carry at least one, preferably at least 3 or 4, or all of the amino acid substitutions Glu(28)->Gln, Lys(31)->Ala, Asn(34)->Asp, Ser(35)->His, Val(36)->Ile and Glu(37)->Thr.

Particularly preferred muteins of the invention carry, when compared to the bilin-binding protein, at least one, at least 4 to 7, or, preferably, at least 8 to 12 of the amino acid substitutions selected from Glu(28)->Gln, Lys (31)->Ala, Asn(34)->Asp, Ser(35)->His, Val(36)->Ile, Glu(37)->Thr, Asn(58)->Arg, His(60)->Ser, Ile(69)->Ser, Leu(88)->Tyr, Tyr(90)->Ile, Lys(95)->Gln, Asn(97)->Gly, Tyr(114)->Phe, Lys(116)->Ser, Gln(125)->Met and Phe(127)->Leu. The representation chosen indicates in each case first the amino acid in the natural bilin-binding protein (SWISS-PROT database accession code P09464, SEQ ID NO: 28) together with the sequence position for the mature polypeptide in brackets, and the corresponding amino acid in a mutein of the invention is stated after the arrow. Very particularly preferred muteins according to this invention carry all of the amino acid substitutions mentioned.

Surprisingly, position 93 of the bilin-binding protein is unchanged in the muteins of the invention, although this amino acid, too, had been affected by the mutagenesis for preparing the random library. Preferred muteins of the bilin-binding protein therefore carry the amino acid Val at said position.

It is an advantage for particular detection methods to use the muteins of the bilin-binding protein of the present invention in a labeled form. Accordingly, this invention further relates to a polypeptide of the invention which is characterized in that it carries at least one label. Suitable labeling groups are known to the skilled worker and include enzyme label, radioactive label, fluorescent label, chromophoric label, (bio)luminescent label or a label containing haptens, biotin, metal complexes, metals or colloidal gold. Very generally, labeling is possible with substances or enzymes which generate a determinable substance in a chemical or enzymatic reaction. In this connection it is possible to couple all known labels for antibodies to the muteins of the invention, too.

A possibility which is particularly advantageous for practical application is to use the inventive muteins of the bilin-binding protein in the form of fusion proteins. Techniques for preparing such fusion proteins by means of genetic engineering methods are known to the skilled worker. Suitable fusion partners for the muteins of the invention would be enzymes and other polypeptides, proteins or protein domains. Such fusions would be suitable for providing the mutein of the bilin-binding protein with additional properties such as, for example, enzymatic activity or affinity for other molecules, such as proteins, macromolecules or low molecular weight ligands.

For example, fusions are possible with enzymes which catalyze chromogenic or fluorogenic reactions or may serve for the release of cytotoxic agents. Further examples for fusion partners which may be advantageous in practice are binding domains such as the albumin-binding domain or the immunoglobulin-binding domain of protein G or protein A, antibody fragments, oligomerization domains, toxins or other binding proteins and functional parts thereof and also affinity peptides such as, for example, the Strep-tag or the Strep-tag II (Schmidt et al., J. Mol. Biol. 255 (1996), 753–766). Suitable fusion partners are also proteins having particular chromogenic or fluorogenic properties, such as, for example, green fluorescent protein. Another suitable fusion partner would be the coat protein III of a filamentous bacteriophage, such as M13, f1 or fd, or a fragment of said coat protein.

Very generally, the term fusion protein is intended here to mean also those inventive muteins of the bilin-binding protein, which are equipped with a signal sequence. Signal sequences at the N-terminus of the polypeptide of the invention may serve for the purpose of directing said polypeptide during biosynthesis into a particular cell compartment, for example the E. coli periplasm or the lumen of the endoplasmic reticulum of a eukaryotic cell, or into the medium surrounding the cell. The signal sequence is typically cleaved off by a signal peptidase. In addition, it is also possible to use other signal or targeting sequences which need not necessarily be located at the N-terminus of the polypeptide and which make it possible to locate said polypeptide in specific cell compartments. A preferred signal sequence for secretion into the E. coli periplasm is the OmpA signal sequence. A large number of further signal sequences and also targeting sequences are known in the prior art.

An advantage of the inventive muteins of the bilin-binding protein is the suitability of both their N-terminus and their C-terminus for preparing fusion proteins. In contrast to antibodies, in which the N-terminus of both the light and the heavy immunoglobulin chain are in spatial proximity to the antigen binding site, it is possible to use in the polypeptides of the invention both ends of the polypeptide chain for the preparation of fusion proteins, without adversely affecting ligand binding.

The invention therefore also relates to fusion proteins of muteins of the bilin-binding protein in which an enzyme, another protein or a protein domain, a signal sequence and/or an affinity peptide is fused to the amino terminus of the polypeptide in an operable manner. The invention yet further relates to fusion proteins of bilin-binding protein muteins or of fusion proteins with the amino terminus of bilin-binding protein muteins in which an enzyme, another protein or a protein domain, a targeting sequence and/or an affinity peptide is fused to the carboxy terminus of the polypeptide in an operable manner.

A preferred enzyme for constructing the fusion proteins of the invention is bacterial alkaline phosphatase (Sowadski et al., J. Mol. Biol. 186 (1985) 417–433), which may be attached either at the N-terminus or at the C-terminus of a mutein of the bilin-binding protein. In addition, such a fusion protein may carry a signal sequence such as, for example, OmpA or PhoA, which effects secretion of said fusion protein into the E. coli periplasm, where the disulfide bonds of the polypeptide chain may form efficiently. Furthermore, it may be equipped with an affinity peptide such as, for example, the Strep-tag II, which allows easy purification of said fusion protein. Specific fusion proteins of the invention are described in the Examples. An advantage of a fusion protein of this kind is its ability to catalyze directly a chromogenic, fluorogenic or chemiluminescent detection reaction, which simplifies its use for detection of the digoxigenin group.

Another advantage of using alkaline phosphatase for constructing fusion proteins of the invention is the fact that this enzyme forms a stable homodimer and, consequently, confers the property of bivalence on the bilin-binding protein mutein as part of the fusion protein. In this way, binding of the digoxigenin group may result in an avidity effect, which increases detection sensitivity. Such an avidity effect can be expected in particular if the digoxigenin-labeled molecule is adsorbed to a solid phase, is present in oligomeric or membrane-bound form or is conjugated with a plurality of digoxigenin groups. Analogously, other homodimeric enzymes are suitable for preparing bivalent fusion proteins containing the inventive muteins of the bilin-binding protein.

Apart from bacterial alkaline phosphatase, it is also possible to use phosphatases from eukaryotic organisms, such as, for example, calf intestine phosphatase (CIP), for preparing fusion proteins of the invention. Said phosphatases are frequently distinguished by higher enzymatic activity (Murphy and Kantrowitz, Mol. Microbiol. 12 (1994), 351–357), which may result in higher detection sensitivity. It is also possible to use mutants of bacterial alkaline phosphatase, which have improved catalytic activity (Mandecki et al., Protein Eng. 4 (1991), 801–804), for constructing fusion proteins of the invention. Other enzymes known to the skilled worker which catalyze chromogenic, fluorogenic or chemiluminescent reactions, such as, for example, β-galactosidase or horseradish peroxidase, are also suitable for preparing fusion proteins of the invention. Moreover, all these enzymes may likewise be employed for labeling muteins of the bilin-binding protein by conjugating them, for example by using common coupling reagents, with the separately obtained mutein or a fusion protein of the mutein.

In another aspect, the present invention relates to a nucleic acid which comprises a sequence coding for a mutein or a fusion protein of a mutein of the bilin-binding protein. This nucleic acid may be part of a vector on which an operatively functional environment for expressing the nucleic acid is present. A large number of suitable vectors is known from the prior art and is not described in detail here. An operatively functional environment means those elements which allow, assist, facilitate and/or increase transcription and/or subsequent processing of an mRNA. Examples of elements of this kind include promoters, enhancers, transcription initiation sites, and transcription termination sites, translation initiation sites, polyadenylation signals, etc. In a preferred embodiment, such nucleic acids of the invention comprise a nucleic acid sequence which encodes the polypeptide sequence depicted as SEQ ID NO: 23. Owing to the degeneracy of the genetic code, it is clear to the skilled worker that the nucleotide sequence stated as SEQ ID NO: 15 represents only a single nucleotide sequence from the group of nucleotide sequences encoding the polypeptide according to SEQ ID NO: 23.

The nucleic acid of the invention or its environment may be designed such that biosynthesis of the polypeptide takes place in the cytosol, in which case the polypeptide sequence being preceded, where appropriate, by a start methionine. In a preferred embodiment, however, an N-terminal signal sequence is used, in particular the OmpA or PhoA signal sequence, in order to direct the polypeptide of the invention into the E. coli periplasm, where the signal sequence is cleaved off by the signal peptidase and the polypeptide chain is able to fold with oxidative formation of the disulfide bonds. Eukaryotic signal sequences may be used in order to secrete the polypeptide of the invention in a eukaryotic host organism.

In principle, both prokaryotic, preferably E. coli, and eukaryotic cells such as, for example, yeasts are considered for expression of the nucleic acid of the invention.

In yet another aspect, the present invention relates to a method for preparing an inventive mutein or fusion protein of a mutein of the bilin-binding protein, which method is characterized in that the nucleic acid coding for the mutein or the fusion protein of a mutein of the bilin-binding protein is expressed in a bacterial or eukaryotic host cell and the polypeptide is obtained from the cell or the culture supernatant. For this purpose, normally a suitable host cell is first transformed with a vector which comprises a nucleic acid coding for a polypeptide of the invention. The host cell is then cultured under conditions under which bio-synthesis of the polypeptide occurs, and the polypeptide of the invention is obtained.

With respect to the preparation method, it must be taken into account that the inventive muteins of the bilin-binding protein have two structural disulfide bonds and that additional disulfide bonds may be present in corresponding fusion proteins. The formation of said disulfide bonds, which takes place during protein folding, is normally ensured if the polypeptide of the invention is directed with the aid of a suitable signal sequence into a cell compartment containing an oxidizing thiol/disulfide redox milieu, for example into the bacterial periplasm or the lumen of the endoplasmic reticulum of a eukaryotic cell. In this respect, the polypeptide of the invention can be liberated by cell fractionation or obtained from the culture supernatant. It is possible, where appropriate, to increase the folding efficiency by overproducing protein disulfide isomerases, for example E. coli DsbC protein, or proteins that assist folding.

On the other hand, it is possible to produce a polypeptide of the invention in the cytosol of a host cell, preferably E. coli. The said polypeptide may then be obtained, for example, in the form of inclusion bodies and afterwards be renatured in vitro. Depending on the intended use, the protein can be purified by means of various methods known to the skilled worker. A suitable method for purifying the inventive muteins of the bilin-binding protein is, for example, affinity chromatography using a column material which carries digoxigenin groups. In order to purify fusion proteins of the muteins of the bilin-binding protein, it is possible to utilize the affinity properties of the fusion protein, which are known from the prior art, for example those of the Strep-tag or the Strep-tag II (Schmidt and Skerra, J. Chromatogr. A 676 (1994), 337–345; Voss and Skerra, Protein Eng. 10 (1997), 975–982), those of the albumin binding domain (Nygren et al., J. Mol. Recogn. 1 (1988), 69–74) or those of alkaline phosphatase (McCafferty et al., Protein Eng. 4 (1991) 955–961). The fact that the muteins of the bilin-binding protein consist only of a single polypeptide chain is advantageous for the methods for preparing the polypeptides of the invention, since no care needs to be taken either of synthesizing several different polypeptide chains within a cell simultaneously or of different polypeptide chains associating with one another in a functional manner.

The possibilities for practical application of the inventive muteins of the bilin-binding protein essentially correspond to those for conventional antibodies or antibody fragments with binding affinity for digoxigenin. Accordingly, the invention also relates to the use of a mutein of the invention or of a fusion protein of a mutein of the bilin-binding protein in a method for detecting, determining, immobilizing or removing digoxigenin or conjugates of digoxigenin with proteins, nucleic acids, carbohydrates, other biological or synthetic macromolecules or low molecular weight chemical compounds.

The inventive muteins of the bilin-binding protein or their fusion proteins can be used in detection methods essentially in a manner analogous to corresponding detection methods known for anti-digoxigenin antibodies and also fragments and/or conjugates thereof. In a further aspect, the present invention therefore relates to a method for detecting the digoxigenin group, in which method a mutein of the bilin-binding protein or a fusion protein of a mutein of the bilin-binding protein is brought into contact with digoxigenin or with digoxigenin conjugates under conditions suitable for effecting binding of the mutein to the digoxigenin group and the mutein or the fusion protein of the mutein is determined.

For this purpose, the mutein may be labeled directly, for example by covalent coupling. It is, however, also possible to use indirect labeling, for example by means of labeled antibodies against the bilin-binding protein or muteins thereof or against domains of fusion proteins of these muteins. The use of inventive fusion proteins containing an enzyme, for example alkaline phosphatase, instead of a labeled mutein of the bilin-binding protein is particularly advantageous. In this case, it is possible to design the determination method with a particularly small number of process steps, whereby, for example, the ability of the enzyme as part of the fusion protein to catalyze a chromogenic, fluorogenic or luminescent detection reaction may be directly utilized. Here, the fact that such fusion proteins are readily available is a particular advantage compared with corresponding fusion proteins of conventional antibodies. Utilization of the above-described avidity effect in the case of an oligomeric fusion protein is a further advantage in such a method.

It is possible to carry out a method for determining the digoxigenin group, for example, for qualitatively detecting nucleic acids conjugated with the digoxigenin group in Southern or Northern blots or proteins conjugated with the digoxigenin group in Western blots. A determination method may also be carried out quantitatively for detecting proteins conjugated with the digoxigenin group in an ELISA. In addition, a determination method of the invention is also suitable for indirect detection of proteins not conjugated with digoxigenin or of other molecules by using a binding protein which is directed against the protein or molecule, for example an antibody or its fragment, and which is conjugated with the digoxigenin group. Indirect detection of the nucleic acids not conjugated with digoxigenin is also possible by using a gene probe which hybridizes with said nucleic acid and which is conjugated with the digoxigenin group. An application in medical diagnostics or therapy results furthermore from the determination of digoxigenin, digoxin, digitoxin or digitoxigenin, without these ligands having to be conjugated with another molecule.

The muteins of the invention or fusion proteins thereof may also be used for immobilizing a molecule conjugated with the digoxigenin group. This immobilization is preferably carried out on solid phases coated with the muteins or their fusion proteins, such as, for example, microtiter plates, immunosticks, microbeads made of organic, inorganic or paramagnetic materials, or sensor surfaces.

Correspondingly, it is likewise possible to use the muteins of the invention or fusion proteins thereof for removing digoxigenin, digoxin, digitoxin or digitoxigenin, or a molecule conjugated with one of these compounds. In this case, in addition to the solid phases mentioned, column materials are also considered for coating with the muteins or their fusion proteins. Preferably, said coating is carried out on suitable column materials by coupling by means of chemically reactive groups. Column materials coated in this way may be used for removing from a solution substances conjugated with digoxigenin groups and also, where appropriate, complexes of such substances with other molecules.

Thus, it is possible, for example, to remove antigens from a solution by adding to the solution antibodies which are directed against the antigens and are conjugated with the digoxigenin group, and contacting the resulting solution with said column material under conditions under which complex formation between the digoxigenin groups and an inventive mutein of the bilin-binding protein or its fusion protein occurs. Following such a removal, it is also possible, where appropriate, to elute the substance conjugated with the digoxigenin. This elution may be carried out by competition with digoxin, digoxigenin, digitoxin or digitoxigenin and also, for example, by lowering or increasing the pH of the solution. In a competitive elution it is possible to utilize in an advantageous manner the higher binding affinity of the muteins of the invention for digitoxigenin or digitoxin compared with the digoxigenin group. In this way it is possible to isolate or purify a substance conjugated with digoxigenin.

The invention is further illustrated by the following Examples and attached drawings, in which:

FIG. 1 represents in each case a fluorescence titration of the Strep-tag II-fused mutein DigA16 with the ligands digoxigenin, digitoxigenin, and ouabain;

FIG. 2 depicts diagrammatically the expression vectors pBBP27 (A) and pBBP29 (B) for preparing fusion proteins of mutein DigA16 with alkaline phosphatase;

FIG. 3 demonstrates quantitative detection of biomolecules conjugated with digoxigenin groups by fusion proteins of mutein DigA16 with alkaline phosphatase in an ELISA;

FIG. 4 shows qualitative detection of biomolecules conjugated with digoxigenin groups by fusion proteins of mutein DigA16 with alkaline phosphatase on a Western blot.

Here, $[P]_t$ corresponds to the total fusion protein concentration used in the particular microtiter plate well. $[P \cdot L]$ is determined on the basis of the enzymatic activity of alkaline phosphatase. The total concentration of digoxigenin groups $[L]_t$, constant within a concentration series, per well and the dissociation constant $K_d$ were fitted as parameters by non-linear regression.

Figure 4:
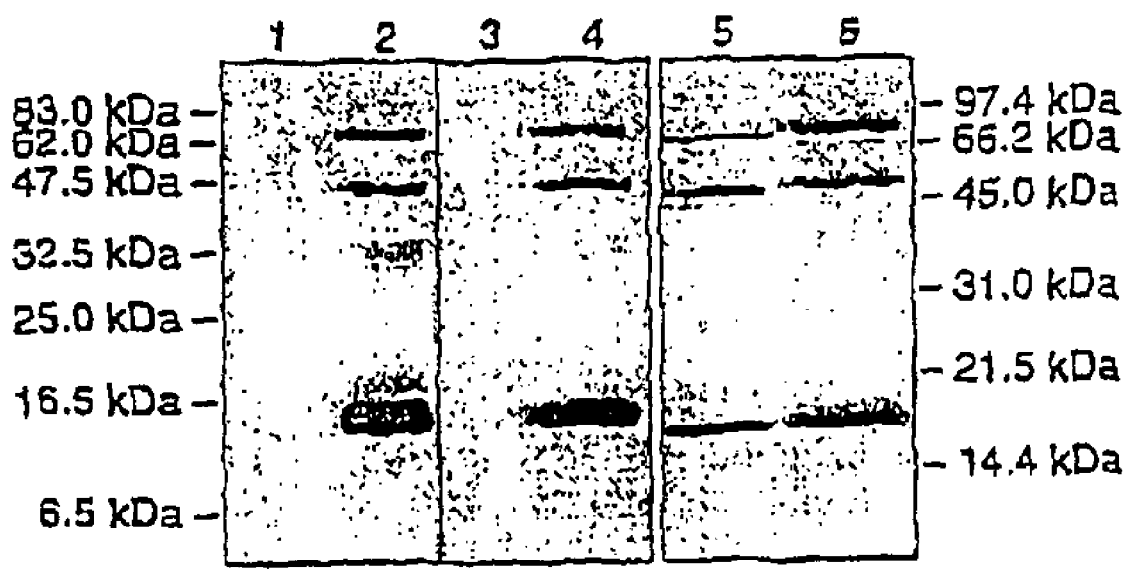

FIG. 4 shows the result of a Western blot experiment from Example 4 for qualitative detection of biomolecules conjugated with digoxigenin groups by means of the mutein DigA16 fusion proteins encoded by pBBP27 (lanes 1 and 2) and pBBP29 (lanes 3 and 4). For comparison, a 15% strength SDS polyacrylamide gel of the biomolecules, stained with Coomassie Brilliant Blue, is also shown (lanes 5 and 6). Here, a mixture of 0.5 $\mu$g of underivatized BSA, underivatized ovalbumin and underivatized RNaseA was fractionated in each case in lanes 1, 3 and 5. A mixture of 0.5 $\mu$g of BSA coupled to digoxigenin groups, ovalbumin coupled to digoxigenin groups and RNaseA coupled to digoxigenin groups was fractionated in each case in lanes 2, 4 and 6.

EXAMPLES

Unless stated otherwise, the genetic engineering methods familiar to the skilled worker, as described, for example, in Sambrook et al. (Molecular Cloning. A Laboratory Manual (1989), Cold Spring Harbor Press) were used.

Example 1

Preparation of a Library for Muteins of the Bilin-Binding Protein, Phagemid Presentation and Selection of a Mutein with Binding Affinity for Digoxigenin A library for muteins of the bilin-binding protein was prepared by subjecting the amino acid sequence positions 34, 35, 36, 37, 58, 60, 69, 88, 90, 93, 95, 97, 114, 116, 125 and 127 of the bilin-binding protein to a concerted mutagenesis in multiple steps by means of the polymerase chain reaction (PCR). The PCR reactions were initially carried out in two separate amplification steps in a volume of in each case 50 µl, and 10 ng of pBBP20 plasmid DNA (SEQ ID NO:1) as template using in each case 25 pmol of two primers (SEQ ID NO:2 and SEQ ID NO:3 in one mixture and SEQ ID NO:4 and SEQ ID NO:5 in a second mixture) which had been synthesized according to the generally known phosphoramidite method were used.

Furthermore, the reaction mixture contained 5 µl of 10xTaq buffer (100 mM Tris/HCl pH 9.0, 500 mM KCl, 1% v/v Triton X-100), 3 µl of 25 mM $MgCl_2$ and 4 µl of dNTP mix (2.5 mM dATP, dCTP, dGTP, dTTP). After filling up with water, the mixture was overlaid with mineral oil and heated to 94° C. in a programmable thermostating block for 2 min. Then 2.5 u of Taq DNA polymerase (5 u/µl, Promega) were added and 20 temperature cycles of 1 min at 94° C., 1 min at 60° C. and 1.5 min at 72° C. were carried out, followed by an incubation at 60° C. for 5 min. The desired amplification products were isolated via preparative agarose gel electrophoresis from low melting point agarose (Gibco BRL), using the Jetsorb DNA extraction kit (Genomed) according to the manufacturer's instructions.

A relevant section of the pBBP20 nucleic acid sequence is shown together with the encoded amino acid sequence as SEQ ID NO:1 and 19, respectively, in the sequence listing. The section starts with a hexanucleotide sequence which was obtained by ligating an XbaI overhang with an SpeI overhang complementary thereto and ends with the HindIII cleavage site. The vector elements outside this region are identical to vector pASK75 whose complete nucleotide sequence is stated in the German Offenlegungsschrift DE 44 17 598 A1.

The subsequent amplification step was carried out in a 100 µl mixture, and in each case approx. 6 ng of the two isolated fragments as template using 50 pmol of each of the two primers SEQ ID NO:6 and SEQ ID NO:7 and also 1 pmol of oligodeoxynucleotide SEQ ID NO:8. The remaining components of the PCR mixture were added in twice the amount, as in the preceding amplification steps. The PCR was carried out in 20 temperature cycles of 1 min at 94° C., 1 min at 55° C., and 1.5 min at 72° C., followed by a final incubation at 60° C. for 5 min. The fragment obtained was again isolated by preparative agarose gel electrophoresis.

For cloning this fragment which represented the mutein library in the form of a mixture of nucleic acids it was first cut with the restriction enzyme BstXI (New England Biolabs) according to the manufacturer's instructions. The nucleic acid fragment obtained (335 base pairs, bp) was purified again by means of preparative agarose gel electrophoresis. Analogously, pBBP20 vector DNA was cut with BstXI and the larger of the two fragments (3971 bp) was isolated.

For ligation, 0.93 µg (4.2 pmol) of the PCR fragment and 11 µg (4.2 pmol) of the vector fragment were incubated in the presence of 102 Weiss units of T4 DNA ligase (New England Biolabs) in a total volume of 500 µl (50 mM Tris/HCl pH 7.8, 10 mM $MgCl_2$, 10 mM DTT, 1 mM ATP, 50 µg/ml BSA) at 16° C. for two days. The DNA was then precipitated by adding 10 µg of yeast tRNA (Boehringer Mannheim), 25 µl of 5 M ammonium acetate and 100 µl of ethanol to in each case 24 µl of the ligation mixture. Incubation at −20° C. for 3 days was followed by centrifugation (25 min, 16000 g, 4° C.). The precipitate was washed in each case with 200 µl of ethanol (70% v/v, −20° C.) and dried under vacuum. Finally, the DNA was taken up in 43.6 µl of TE/10 (1 mM Tris/HCl pH 8.0, 0.1 mM EDTA). The DNA concentration of the solution obtained was estimated by analytical agarose gel electrophoresis on the basis of the fluorescence intensity of the bands stained with ethidium bromide in comparison with a DNA size standard of known concentration.

Preparation of electrocompetent cells of the *E. coli* K12 strain XL1-Blue (Bullock et al., BioTechniques 5 (1987), 376–379) was carried out according to the methods described by Tung and Chow (Trends Genet. 11 (1995), 128–129) and by Hengen (Trends Biochem. Sci. 21 (1996), 75–76). 1 l of LB medium was adjusted to an optical density at 600 nm, $OD_{600}$=0.08 by adding a stationary XL1-Blue overnight culture and incubated in a 3 l Erlenmeyer flask at 200 rpm and 26° C. After reaching $OD_{600}$=0.6, the culture was cooled on ice for 30 min and then centrifuged at 4000 g and 4° C. for 15 min. The cell sediment was washed twice with in each case 500 ml of ice cold 10% w/v glycerol and finally resuspended in 2 ml of ice cold GYT medium (10% w/v glycerol, 0.125% w/v yeast extract, 0.25% w/v tryptone).

Electroporation was carried out by using the Easyjec T Basic system (EquiBio) with the corresponding cuvettes (electrode distance 2 mm). All operational steps were carried out in a cold room at 4° C. 5 to 6 µl of the above-described DNA solution (245 ng/µl) were in each case mixed with 40 µl of the cell suspension, incubated on ice for 1 min and then transferred into the cuvette. After electroporation, the suspension was immediately diluted in 2 ml of fresh ice-cold SOC medium (2% w/v tryptone, 0.5% w/v yeast extract, 10 mM NaCl, 10 mM $MgSO_4$, 10 mM $MgCl_2$) and agitated at 37° C. and 200 rpm for 60 min. The cells were then sedimented at 3600 g for in each case 2 min, resuspended in 1 ml of LB medium containing 100 µg/ml of ampicillin (LB/Amp) and plated out at 200 µl each on agar plates (140 mm in diameter) with LB/Amp medium. Using a total of 10.7 µg of the ligated DNA in eight electroporation mixtures produced in this way $3.73 \cdot 10^8$ transformants which were distributed on 40 agar plates.

After incubation at 32° C. for 14 h, the colonies obtained in this way were scraped off the agar plates with the addition of in each case 10 ml of 2xYT/Amp medium, transferred to a sterile Erlenmeyer flask and agitated at 37° C., 200 rpm for 20 min to complete resuspension. 50 ml of 2xYT/Amp medium prewarmed to 37° C. were inoculated with 2.88 ml of said suspension so that the cell density was 1.0 $OD_{550}$. This culture was incubated at 37° C., 160 rpm for 6 h to reach a stationary cell density, and phasmid DNA was isolated with the aid of the plasmid Midi kit (Qiagen) according to the manufacturer's instructions. Finally, the DNA was taken up in 100 µl of TE (10 mM Tris/HCl pH 8.0, 1 mM EDTA) and stored at 4° C. for further use.

In order to prepare a library of recombinant phagemids (Kay et al., Phage Display of Peptides and Proteins—A Laboratory Manual (1996), Academic Press) which carry the muteins of the bilin-binding protein as a fusion with the truncated coat protein pIII, the phasmid DNA obtained in this way was used for transformation of electrocompetent cells of E. coli XL1-Blue. Electroporation was carried out as described above with the aid of the Easyjec T Basic system. In a total of 13 mixtures, 40 µl of the cell suspension of electrocompetent cells were in each case transformed with in each case 2 µg of the DNA in a volume of 5 µl. After electroporation, the cell suspension obtained from each mixture was diluted immediately in 2 ml of fresh ice-cold SOC medium and agitated at 37° C. and 200 rpm for 60 min.

The mixtures were combined (volume=26 ml) and 74 ml of 2xYT medium and 100 µl of ampicillin (stock solution 100 mg/ml, final concentration 100 mg/l) were added. The total number of transformants obtained was estimated at $1.1 \cdot 10^{10}$ by plating out 100 µl of a $1:10^5$ dilution of the obtained suspension on agar plates containing LB/Amp medium. After incubation at 37° C. and 160 rpm for 60 min, the culture was infected with 500 µl of VCS-M13 helper phage ($1.1 \cdot 10^{12}$ pfu/ml, Stratagene) and agitated at 37° C., 160 rpm for a further 60 min. Subsequently, 200 µl of kanamycin (stock solution 35 mg/ml, final concentration 70 mg/l) were added, the incubator temperature was lowered to 26° C. and, after 10 min, anhydrotetracycline (50 µl of a 50 µg/ml stock solution in dimethylformamide, final concentration 25 µg/l) was added to induce gene expression. Finally, for production of the phagemids the culture was incubated at 26° C., 160 rpm for 7 h.

The cells were removed by centrifugation of the culture (15 min, 12000 g, 4° C.). The supernatant containing the phagemid particles was sterile-filtered (0.45 µm), mixed with ¼ volume (25 ml) of 20% w/v PEG 8000, 15% w/v NaCl and incubated at 4° C. overnight. After centrifugation (20 min, 18000 g, 4° C.), the precipitated phagemid particles were dissolved in a total of 4 ml of cold PBS (4 mM $KH_2PO_4$, 16 mM $Na_2HPO_4$, 115 mM NaCl, pH 7.4). The solution was incubated on ice for 30 min and distributed into four 1.5 ml reaction vessels at equal volumes. After removing undissolved components by centrifugation (5 min, 18500 g, 4° C.), the supernatant was transferred in each case to a new reaction vessel.

The phagemid particles were again precipitated by mixing with ¼ volume (in each case 0.25 ml per reaction vessel) of 20% w/v PEG 8000, 15% w/v NaCl and incubating on ice for 60 min. After centrifugation (20 min, 18500 g, 4° C.), the supernatant was removed and the precipitated phagemid particles were each dissolved in 0.5 ml of PBS. After incubation on ice for 30 min, centrifugation (5 min, 18500 g, 4° C.) was repeated to clarify the solution. The supernatant containing the phagemid particles (between $1 \times 10^{12}$ and $4 \times 10^{12}$ cfu/ml) was then used for affinity enrichment.

For affinity enrichment of the recombinant phagemids presenting the muteins of the bilin-binding protein Immuno-Sticks (NUNC) were used. These were coated overnight with 800 µl of a conjugate (100 µg/ml) of ribonuclease A (RNaseA) and digoxigenin in PBS.

The conjugate was prepared by adding 1.46 µmol (0.96 mg) of digoxigenin-3-O-methylcarbonyl-ε-aminocaproic acid N-hydroxysuccinimide ester (DIG-NHS, Boehringer Mannheim) in 25 µl of dimethyl sulfoxide (DMSO) in µl steps and with constant mixing to 0.73 µmol (10 mg) of RNaseA (Fluka) in 1 ml of 5% w/v sodium hydrogen carbonate. The mixture was incubated with stirring at room temperature (RT) for 1 h. Excess reagent was then removed from the RNaseA conjugate by means of a PD-10 gel filtration column (Pharmacia) according to the manufacturer's instructions.

Unoccupied binding sites on the Immuno-Stick surface were saturated by incubation with 1.2 ml of 2% w/v BSA in PBST (PBS with 0.1% v/v Tween 20) at RT for 2 h. After three short washes with in each case 1.2 ml of PBST, the Immuno-Stick was incubated in a mixture of 250 µl of phagemid solution and 500 µl of blocking buffer (2% w/v BSA in PBST) at RT for 1 h.

For removing unbound phagemids the solution was stripped off and the Immuno-Stick was washed eight times with in each case 950 µl of PBST for 2 min. Finally, adsorbed phagemids were competitively eluted during a 15 min incubation of the Immuni-Stick with 950 µl of a 2 mM solution of digoxigenin in PBS (for this purpose, 0.742 mg of digoxigenin (Fluka) were dissolved in 19.2 µl of N,N-dimethylformamide (DMF) and added to 930.8 µl of PBS).

The phagemids were propagated by heating 950 µl of solution of the elution fraction obtained (between $10^6$ and $10^8$ colony-forming units, depending on the selection cycle) briefly to 37° C., mixing the solution with 4 ml of an exponentially growing culture of E. coli XL1-Blue ($OD_{550}$=0.5) and incubated at 37° C., 200 rpm for 30 min. The phagemid-infected cells were then sedimented (2 min, 4420 g, 4° C.), resuspended in 800 µl of fresh 2xYT medium and plated out on four agar plates containing LB/Amp medium (140 mm in diameter) After incubation at 32° C. for 14 h, the colonies obtained in this way were scraped off the agar plates with the addition of in each case 10 ml of 2xYT/Amp medium, transferred to a sterile Erlenmeyer flask and agitated at 37° C., 200 rpm for 20 min to complete resuspension.

For repeated production and affinity enrichment of phagemid particles 50 ml of 2xYT/Amp medium prewarmed to 37° C. were inoculated with 0.2 to 1 ml of said suspension so that the cell density was $OD_{550}$=0.08. This culture was incubated at 37° C., 160 rpm to a cell density of $OD_{550}$=0.5, infected with 250 µl of VCS-M13 helper phage ($1.1 \cdot 10^{12}$ pfu/ml, Stratagene), and the procedure was continued as already described above.

The phagemids obtained from the first affinity concentration were used to carry out a series of eight further enrichment cycles using Immuno-Sticks which had been freshly coated with the digoxigenin-RNaseA conjugate. The phagemids obtained after the last enrichment cycle were again used for infecting E. coli XL1-Blue. The mixture of the colonies obtained was scraped off the agar plates using 2xYT/Amp medium and resuspended, as described above. This cell suspension was used to inoculate 50 ml of 2xYT/Amp medium, and the phasmid DNA was isolated using the QIAprep Spin Miniprep kit (QIAGEN) according to the manufacturer's instructions.

In order to be able to produce the muteins of the bilin-binding protein as a fusion protein with the Strep-tag II and the albumin-binding domain, the gene cassette between the two BstXI cleavage sites was subcloned from vector pBBP20 into vector pBBP22. A relevant section of the pBBP22 nucleic acid sequence is represented, together with the encoded amino acid sequence, as SEQ ID NO:9 and 20, respectively, in the sequence listing. The section starts with the XbaI cleavage site and ends with the HindIII cleavage site. The vector elements outside this region are identical to vector pASK75.

For this purpose, the DNA isolated from the mixture of the E. coli colonies was cut with restriction enzyme BstXI, and the smaller of the two fragments (335 bp) was purified by preparative agarose gel electrophoresis as described above. In the same manner, pBBP22 vector DNA was cut with BstXI and the larger of the two fragments (3545 bp) was isolated.

1.5 Weiss units of T4 DNA ligase (Promega) were added to 50 fmol of each of the two DNA fragments in a total volume of 20 µl (30 mM Tris/HCl pH 7.8, 10 mM $MgCl_2$, 10 mM DTT, 1 mM ATP) and the mixture was incubated for ligation at 16° C. overnight. 5 µl of this ligation mixture were used to transform 200 µl of competent cells of E. coli strain TG1-F⁻ according to the $CaCl_2$ method (Sambrook et al., supra), and 2.2 ml of a cell suspension were obtained.

The transformants were then screened for production of muteins with binding activity for the digoxigenin group by means of a colony screening assay. For this purpose, a cut-to-fit hydrophilic PVDF membrane (Millipore, type GVWP, pore size 0.22 µm) marked at one position was placed on an LB/Amp agar plate. 150 µl of the cell suspension from the transformation mixture were plated out evenly on said membrane, and approx. 500 colonies were obtained. The plate was incubated in an incubator at 37° C. for 7.5 h until the colonies were approx. 0.5 mm in diameter.

In the meantime, a hydrophobic membrane (Millipore, Immobilon P, pore size 0.45 µm) which had likewise been cut to fit was wetted with PBS according to the manufacturer's instructions. Said membrane was then gently agitated in a solution of 10 mg/ml of human serum albumin (HSA, Sigma) in PBS at RT for 4 h. Remaining binding sites on the membrane were saturated by incubation with 3% w/v BSA, 0.5% v/v Tween 20 in PBS at RT for 2 h. The membrane was washed with 20 ml of PBS for two times for 10 min and then gently agitated in 10 ml of LB/Amp medium to which 200 µg/l of anhydrotetracycline had been added for 10 min. Said membrane was then marked at one position and placed on a culture plate with LB/Amp agar which additionally contained 200 µg/l of anhydrotetracycline.

The previously obtained hydrophilic membrane on which colonies had grown was then placed onto the hydrophobic membrane such that the two markings coincided. The culturing plate with the two membranes was incubated at 22° C. for 15 h. During this phase, the particular muteins were secreted by the colonies as fusion proteins and immobilized on the lower membrane by means of complex formation between the albumin-binding domain and the HSA.

Subsequently, the upper membrane containing the colonies was transferred to a fresh LB/Amp agar plate and stored at 4° C. The hydrophobic membrane was removed, washed with 20 ml of PBST for three times 10 min and then incubated in 10 ml of a 10 µg/ml solution of a conjugate of BSA with digoxigenin in PBST for 1 h.

The conjugate of BSA (Sigma) and digoxigenin was prepared by adding a solution of 3.0 µmol (1.98 mg) of DIG-NHS in 25 µl of DMSO in µl steps and with constant mixing to 300 nmol (19.88 mg) of BSA (Sigma) in 1.9 ml of 5% w/v sodium hydrogen carbonate. The mixture was incubated with stirring at RT for 1 h and excess reagent was removed from the BSA conjugate by means of a PD-10 gel filtration column according to the manufacturer's instructions.

In order to detect bound digoxigenin-BSA conjugate, the membrane was incubated, after washing twice in 20 ml of PBST, with 10 ml of anti-digoxigenin Fab-alkaline phosphatase conjugate (Boehringer Mannheim, diluted 1:1000 in PBST) for 1 h. The membrane was then washed twice with 20 ml PBST and twice with 20 ml of PBST for in each case 5 min and gently agitated in AP buffer (0.1 M Tris/HCl pH 8.8, 0.1 M NaCl, 5 mM $MgCl_2$) for 10 min. For the chromogenic detection reaction, the membrane was incubated in 10 ml of AP buffer to which 30 µl of 5-bromo-4-chloro-3-indolyl phosphate, p-toluidinium salt (BCIP, Roth, 50 µg/ml in dimethylformamide) and 5 µl of Nitro Blue Tetrazolium (NBT, Sigma, 75 µg/ml in 70% v/v dimethylformamide) had been added, until at the positions of some of the colonies distinct color signals became visible. In this way, digoxigenin-binding activity of the bilin-binding protein muteins which had been produced in the form of fusion proteins with Strep-tag and ABD by said colonies was detected.

Four colonies from the upper membrane, which caused a distinct color signal, were used for preparing cultures in LB/Amp medium of 4 ml in volume. Their plasmid DNA was isolated with the aid of the JETquick Plasmid Miniprep Spin kit (Genomed) according to the manufacturer's instructions, and the gene section coding for the mutein was subjected to sequence analysis. Sequence analysis was carried out with the aid of the T7 sequencing kit (Pharmacia) according to the manufacturer's instructions by using oligodeoxynucleotides SEQ ID NO:10 and SEQ ID NO:11. It was found in the process that all four plasmids studied carried the same nucleotide sequence. The corresponding gene product was denoted by DigA (SEQ ID NO:12). The DigA nucleotide sequence was translated into the amino acid sequence (SEQ ID NO: 21) and is represented in the sequence listing.

Example 2

Partial Random Mutagenesis of the DigA Mutein and Selection of Muteins with Improved Binding Affinity for Digoxigenin In order to improve the affinity between the DigA mutein and digoxigenin, which was determined as 295±36 nM according to Example 3, the 6 amino acid positions 28, 31 and 34–37 in DigA were selected for a more substantial partial random mutagenesis.

For mutating said positions the PCR was carried out using a degenerated oligodeoxynucleotide primer. The amplification reaction was carried out in a total volume of 100 µl, with 2 ng of the vector pBBP22 plasmid DNA coding for DigA (SEQ ID NO:12) being used as template. The reaction mixture contained 50 pmol of the two primers SEQ ID NO:13 and SEQ ID NO:7 and also the other components according to the method described in Example 1. The PCR was carried out in 20 temperature cycles of 1 min at 94° C., 1 min at 65° C., and 1.5 min at 72° C., followed by a final incubation at 60° C. for 5 min. The DNA fragment obtained was isolated by preparative agarose gel electrophoresis and then cut with BstXI according to the manufacturer's instructions. The resulting DNA fragment of 335 bp in length was again purified by preparative agarose gel electrophoresis.

The pBBP24 vector DNA was cut with BstXI accordingly and the 4028 bp fragment obtained was isolated. A relevant section of the pBBP24 nucleic acid sequence is represented, together with the encoded amino acid sequence, as SEQ ID NO:14 and 22, respectively in the sequence listing. The section starts with the XbaI cleavage site and ends with the HindIII cleavage site. The vector elements outside this region are identical to vector pASK75. PBBP24 is virtually identical with pBBP20, wherein the BBP gene has been inactivated by means of appropriately introduced stop codons.

1.3 μg of the cleaved DNA fragment from the PCR and 16.0 μg of the pBBP24 fragment were incubated for ligation in the presence of 120 Weiss units of T4 DNA ligase (New England Biolabs) in a total volume of 600 μl (50 mM Tris/HCl pH 7.8, 10 mM MgCl$_2$, 10 mM DTT, 1 mM ATP, 50 μg/ml BSA) at 16° C. for 18 h. The DNA was then precipitated by adding 10 μg of yeast tRNA (Boehringer Mannheim), 25 μl of 5 M ammonium acetate and 100 μl of ethanol to in each case 24 μl of the ligation mixture. Incubation at −20° C. for two weeks was followed by centrifugation (20 min, 16000 g, 4° C.). The precipitate was washed in each case with 150 μl of ethanol (70% v/v, −20° C.) and dried under vacuum. Finally, the DNA was taken up in 80 μl of TE/10.

E. coli XL1-Blue cells were transformed with the ligated DNA by electroporation according to the procedure described in Example 1, with in each case 40 μl of cell suspension of electrocompetent cells being mixed with 5 μl of the DNA solution in 16 mixtures. After electroporation, the cells were immediately diluted in 2 ml of fresh ice-cold SOC medium and agitated at 37° C. and 200 rpm for 60 min.

168 ml of 2xYT medium and 200 μl of ampicillin (stock solution 100 mg/ml, final concentration 100 mg/l) were added to the combined suspensions. The total number of transformants obtained was estimated at $1.48 \cdot 10^9$ by plating out 100 μl of a $1:10^4$ dilution of the obtained cell suspension on agar plates. After incubation at 37° C. and 160 rpm for 60 min, the transformants were infected with 4 ml of VCS-M13 helper phage ($6.3 \cdot 10^{11}$ pfu/ml, Stratagene) and agitated at 37° C. and 160 rpm for a further 30 min. Subsequently, 400 μl of kanamycin (stock solution 35 mg/ml, final concentration 70 mg/l) were added, the incubator temperature was lowered to 26° C. and, after 10 min, anhydrotetracycline (100 μl of a 50 μg/ml stock solution in dimethylformamide, final concentration 25 μg/l) was added to induce gene expression. Finally, the phagemids were produced by incubating the culture at 26° C. and 160 rpm for 7 h. The cells were removed and the phagemids purified by precipitation as described in Example 1.

Streptavidin-coated paramagnetic particles (Dynabeads M-280 Streptavidin, Dynal) were used together with a double conjugate of BSA with digoxigenin and biotin for affinity enrichment from the library of phagemids which presented the partially mutated DigA mutein.

A double conjugate of BSA with digoxigenin and biotin was prepared by adding 1.5 μmol (0.99 mg) of DIG-NHS in 12.5 μl of DMSO and 1.5 μmol (0.68 mg) of D-biotinoyl-ε-aminocaproic acid N-hydroxysuccinimide ester (Boehringer Mannheim) in 12.5 μl of DMSO in μl steps and with constant mixing to 300 nmol (19.88 mg) of BSA in 1.9 ml of 5% w/v sodium hydrogen carbonate. The mixture was incubated with stirring at RT for 1 h. Excess reagent was removed from the double conjugate via a PD-10 gel filtration column according to the manufacturer's instructions.

In order to enrich Digoxigenin-binding phagemids, 40 μl of a 0.5 μM solution of the double conjugate (33.5 μg/ml) in PBS were mixed with 260 μl of a solution of the freshly prepared phagemids (between $5 \cdot 10^{11}$ and $5 \cdot 10^{12}$ cfu/ml) and incubated at RT for 1 h so that the complex formation between the digoxigenin group and the muteins presented by the phagemids was able to occur. This was followed by adding 100 μl of a solution of 8% w/v BSA, 0.4% v/v Tween 20 in PBS.

Parallel thereto, 100 μl of the commercially available suspension of paramagnetic particles were washed with three times 100 μl of PBS. Here, the particles were kept suspended for 1 min by rotating the 1.5 ml Eppendorf vessel and then collected at the wall of the Eppendorf vessel with the aid of a magnet, and the supernatant was stripped off. In order to saturate unspecific binding sites, the paramagnetic particles were incubated with 100 μl of 2% w/v BSA in PBST at RT for 1 h. After removing the supernatant, the mixture of double conjugate and phagemids was added to the paramagnetic particles, and the particles were resuspended and incubated at RT for 10 min. Finally, free biotin-binding sites of Streptavidin were saturated by adding 10 μl of a 4 μM D-desthiobiotin (Sigma) solution in PBS to the mixture and incubating said mixture at RT for 5 min. This procedure also prevented the Strep-tag II as part of the fusion protein of the muteins and the phage coat protein pIII fragment from being able to form a complex with Streptavidin.

Unbound phagemids were removed by washing the paramagnetic particles eight times with 1 ml of fresh PBST with the addition of 1 mM D-desthiobiotin, the particles were collected with the aid of the magnet and the supernatant was stripped off. The bound phagemids were eluted by incubating the resuspended particles in 950 μl of 0.1 M glycine/HCl pH 2.2 for 15 minutes. After collecting the particles on the magnet, the supernatant was again stripped off and this was immediately followed by neutralizing the pH of said solution by addition of 140 μl of 0.5 M Tris.

The phagemids were propagated by mixing the elution fraction obtained, according to the procedure in Example 1, with 4 ml of an exponentially growing culture of E. coli XL1-Blue (OD$_{550}$=0.5) and incubating at 37° C., 200 rpm for 30 min. The phagemid-infected cells were then sedimented (2 min, 4420 g, 4° C.), resuspended in 800 μl of fresh 2xYT medium and plated out on four agar plates containing LB/Amp medium (140 mm in diameter). After incubation at 32° C. for 14 h, the colonies obtained in this way were scraped off the agar plates with the addition of in each case 10 ml of 2xYT/Amp medium, transferred to a sterile Erlenmeyer flask and agitated at 37° C., 200 rpm for 20 min to complete resuspension.

For repeated production and affinity enrichment of phagemid particles 50 ml of 2xYT/Amp medium prewarmed to 37° C. was inoculated with 0.2 to 1 ml of said suspension so that the cell density was OD$_{550}$=0.08. This culture was incubated at 37° C., 160 rpm to a cell density of OD$_{550}$=0.5 and infected with 300 μl of VCS-M13 helper phage ($6.3 \cdot 10^{11}$ pfu/ml, Stratagene). The affinity selection was then repeated using the paramagnetic particles and the digoxigenin/biotin double conjugate under the abovementioned conditions. A total of 4 selection cycles were carried out in this way.

The phagemids obtained after the last concentration cycle were again used for infecting E. coli XL1-Blue. The mixture of the obtained colonies which had been scraped off the agar plates using 2xYT/Amp medium and had been resuspended, as described above, was used to inoculate 50 ml of 2xYT/Amp medium, and phasmid DNA was isolated using the QIAprep spin miniprep kit (QIAGEN) according to the manufacturer's instructions.

Subsequently, the gene cassette between the two BstXI cleavage sites was subcloned, as in Example 1, from vector pBBP24 into vector pBBP22, and competent cells of E. coli strain TG1-F$^-$ were transformed according to the CaCl$_2$ method. Finally, the transformants were, again according to Example 1, screened for production of muteins with binding activity for the digoxigenin group by means of the colony screening assay.

Seven of the colonies showing a strong signal intensity in the colony screening assay were cultured. Their plasmid DNA was isolated by means of the plasmid miniprep spin kit (Genomed) according to the manufacturer's instructions, and the gene section coding for the mutein was subjected to sequence analysis as in Example 1. It was found in the process that all plasmids studied had different sequences. After translating the nucleotide sequences into amino acid sequences, six of the seven variants studied had an amber stop codon at amino acid position 28. However, this stop codon was at least partially suppressed when choosing suitable amber-suppressor strains such as, for example, *E. coli* XL1-Blue or TG1-F⁻ and instead translated as glutamine. Thus a full-length functional protein was produced both during affinity enrichment and in the colony screening assay.

As the only mutein without an amber stop codon among the muteins found, the mutein with SEQ ID NO:15 was particularly well suited for bacterial production. Consequently, this mutein, also denoted by DigA16, was characterized in more detail with regard to its ability to bind to the digoxigenin group.

Example 3

Production of the DigA and DigA16 Muteins and Determination of their Affinity for Digoxigenin and Derivatives Thereof by Fluorescence Titration For preparative production of the bilin-binding protein muteins obtained from the previous Examples the coding gene section between the two BstXI cleavage sites was sublcloned from the type pBBP22 vector into the expression plasmid pBBP21. The plasmid thus obtained coded for a fusion protein of the OmpA signal sequence, followed by the mutein and the Strep-tag II affinity tag.

A relevant section of the pBBP21 nucleic acid sequence is represented, together with the encoded amino acid sequences, as SEQ ID NOS 16, 24 and 25, respectively, in the sequence listing. The section starts with the XbaI cleavage site and ends with a hexanucleotide which was obtained by ligating a blunt strand end with a filled-up HindIII strand end, with the loss of the original HindIII cleavage site. The vector elements outside this region are identical to vector pASK75.

For subcloning, the plasmid DNA coding for the relevant mutein was cut with restriction enzyme BstXI, and the smaller of the two fragments (335 bp) was purified by preparative agarose gel electrophoresis as described in Example 1. In the same manner, pBBP21 vector DNA was cut with BstXI, and the larger of the two fragments (4132 bp) was isolated.

1.5 Weiss units of T4 DNA ligase (Promega) were added to 50 fmol of each of the two DNA fragments in a total volume of 20 $\mu$l (30 mM Tris/HCl pH 7.8, 10 mM MgCl$_2$, 10 mM DTT, 1 mM ATP) and the mixture was incubated for ligation at 16° C. for 16 h. 5 $\mu$l of the ligation mixture were then used to transform *E. coli* JM83 (Yanisch-Perron et al., Gene 33 (1985), 103–119) according to the CaCl$_2$ method, wherein 2.2 ml of a cell suspension were obtained. 100 $\mu$l of this suspension were plated out on an agar plate containing LB/Amp medium and incubated at 37° C. for 14 h.

For protein production, one of the obtained single colonies was selected, a 50 ml preculture (LB/Amp medium) was inoculated with this colony and incubated at 30° C. and 200 rpm overnight. 40 ml of the preculture were then transferred by inoculating 2 l of LB/Amp medium in a 5 l Erlenmeyer flask, followed by incubating the culture at 22° C. and 200 rpm. At a cell density of OD$_{550}$=0.5, gene expression was induced by adding 200 $\mu$g/l anhydrotetracycline (200 $\mu$l of a 2 mg/ml stock solution in DMF), followed by agitating at 22° C., 200 rpm for a further 3 h.

The cells were removed by centrifugation (15 min, 4420 g, 4° C.) and, after removing the supernatant, resuspended in 20 ml of periplasm lysis buffer (100 mM Tris/HCl pH 8.0, 500 mM sucrose, 1 mM EDTA) with cooling on ice. After incubation on ice for 30 min, the spheroplasts were removed in two successive centrifugation steps (15 min, 4420 g, 4° C. and 15 min, 30 000 g, 4° C.). The periplasmic protein extract obtained in this way was dialyzed against SA buffer (100 mM Tris/HCl pH 8.0, 150 mM NaCl, 1 mM EDTA), sterile-filtered and used for chromatographic purification.

Purification was carried out by means of the Strep-tag II affinity tag (Schmidt and Skerra, Protein Eng. 6 (1993), 109–122) fused to the C-terminus of the muteins. In the present case, Streptavidinmutein "1" was used (Voss and Skerra, Protein Eng. 10 (1997), 975 –982), which was coupled to activated Sepharose (with 5 mg/ml immobilized Streptavidin with respect to the bed volume of the matrix).

A chromatography column packed with 2 ml of said material was equilibrated at 4° C. and a flow rate of 20 ml/h with 10 ml of SA buffer. The chromatography was monitored by measuring absorption of the eluate at 280 nm in a flow-through photometer. Application of the periplasmic protein extract was followed by washing with SA buffer until the base line was reached. Bound mutein was then eluted with 10 ml of a solution of 2.5 mM D-desthiobiotin (Sigma) in SA buffer. The fractions containing the purified mutein were checked by means of SDS polyacrylamide gel electrophoresis (Fling and Gregerson, Anal. Biochem. 155 (1986), 83–88) and combined. The protein yields were between 200 $\mu$g and 800 $\mu$g per 2 l culture.

The ligand binding properties of muteins DigA, DigA16 and also of the recombinant bilin-binding protein (encoded by SEQ ID NO:16) were determined by means of the method of fluorescence titration. In this case, the decrease in intrinsic tyrosine and/or tryptophan fluorescence of the protein forming a complex with the ligand was measured. The measurements were carried out in a fluorimeter, type LS 50 B (Perkin Elmer) at an excitation wavelength of 295 nm (slit width 4 nm) and an emission wavelength of 345 nm (slit width 6 nm). The ligands used were digoxigenin (Fluka), digoxin (Fluka), digitoxigenin (Fluka), digitoxin (Fluka), testosterone (Sigma), ouabain (Fluka), and 4-aminofluorescein (Fluka). The ligands showed no significant intrinsic fluorescence or absorption at the stated wavelength.

The buffer system used was PBS with the addition of 1 mM EDTA. The solution of the relevant purified mutein was dialyzed four times against this buffer and adjusted to a concentration of 1 $\mu$M by dilution. All solutions used were sterile-filtered (Filtropur S 0.45 $\mu$m, Sarstedt). The concentration was determined by means of absorption at 280 nm using calculated extinction coefficients of 53580 M$^{-1}$ cm$^{-1}$ for DigA and DigA16 (Wisconsin Software Package, Genetics Computer Group). For Bbp, the calculated extinction coefficient of 54150 M$^{-1}$ cm$^{-1}$, corrected in the presence of guanidinium chloride according to Gill and von Hippel (Anal. Biochem. 182 (1989), 319–326) was used.

For the measurement, 2 ml of the mutein solution were introduced into a quartz cuvette equipped with a magnetic stirrer bar and thermally equilibrated at 25° C. in the sample holder of the photometer. Then a total of 40 μl of a 100 μM to 500 μM solution of the ligand in the same buffer were pipetted in steps of from 1 μl to 4 μl. The dilution of the introduced protein solution by altogether no more than 2%, which took place in the process, was not taken into account in the subsequent evaluation of the data. After each titration step, the equilibrium was allowed to reach by incubating with stirring for 1 min, and the fluorescence signal was measured as average over 10 s. After subtracting the fluorescence value of the buffer, the signals were normalized to an initial value of 100%.

The thus obtained data of a titration series were fitted by nonlinear regression using the computer program Kaleidagraph (Abelbeck Software) according to the following equation $$F = ([P]_t - [L]_t - K_d)\frac{f_P}{2} + ([P]_t + [L]_t + K_d)\frac{f_{PL}}{2} + (f_P - f_{PL})\sqrt{\frac{([P]_t + [L]_t + K_d)^2}{4} - [P]_t[L]_t}$$

Here, F means the normalized fluorescence intensity and $[L]_t$ the total ligand concentration in the particular titration step. $[P]_t$ as mutein concentration, $f_{PL}$ as fluorescence coefficient of the mutein-ligand complex and $K_d$ as the thermodynamic dissociation constant of said complex were fitted as free parameters to the normalized data.

Figure 1:
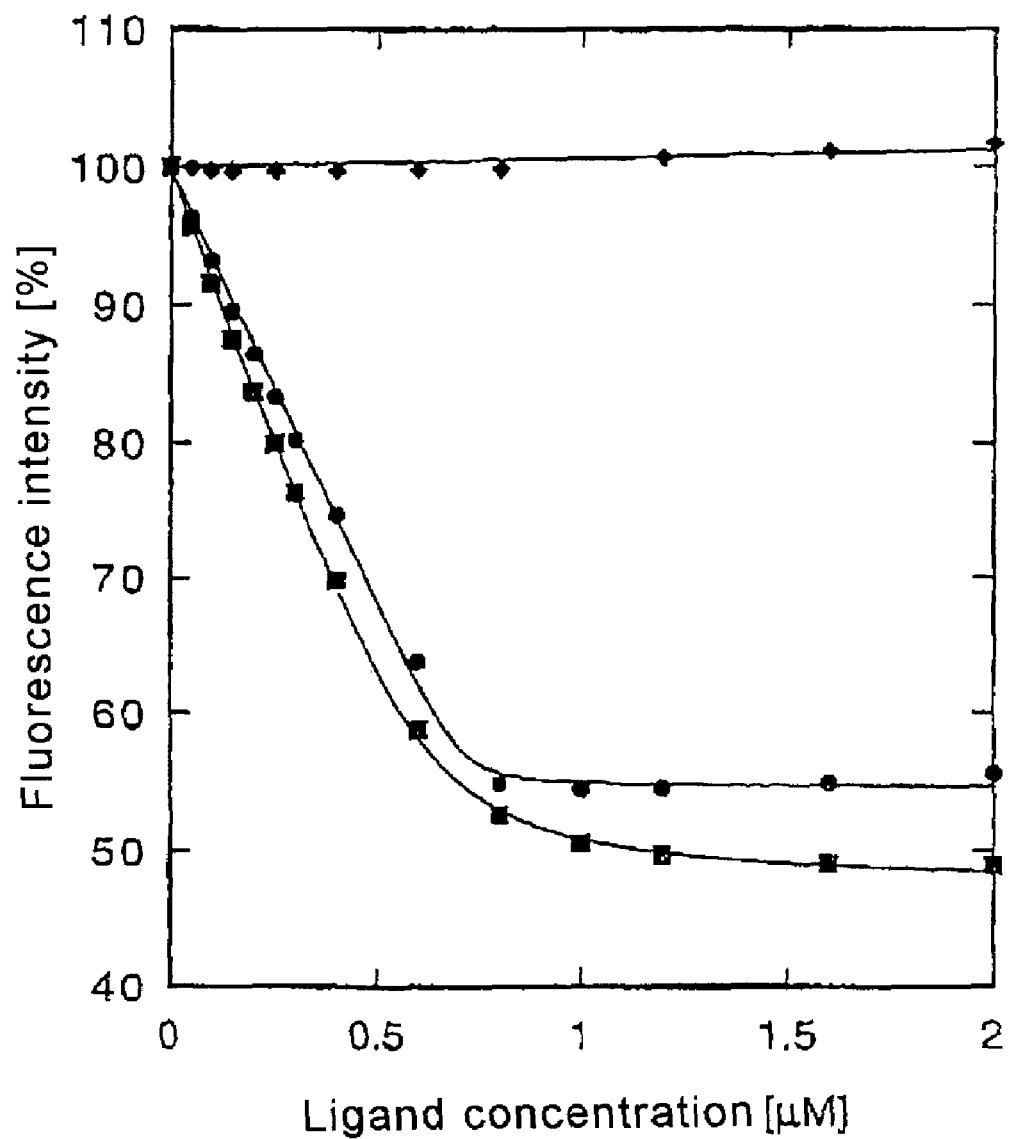
FIG. 1 shows the graphic representation of results from Example 3 in which different concentrations of the steroids digoxigenin (squares), digitoxigenin (circles) and ouabain (rhomboids) were added to a 1 $\mu$M solution of mutein DigA16. The particular protein fluorescence intensities were measured at an excitation wavelength of 295 nm and an emission wavelength of 345 nm and plotted as a function of the actual total steroid concentration in the particular reaction mixture. Finally, the data points were fitted to a regression curve by means of non-linear regression.

FIG. 1 represents graphically the results of the fluorescence titrations of the DigA16 mutein with the ligands digoxigenin, digitoxigenin and ouabain. It turns out that digitoxigenin is bound even tighter than digoxigenin, while no binding is observed for ouabain.

The values resulting from the fluorescence titrations for the dissociation constants of the complexes of the bilin-binding protein muteins and the various ligands are summarized in the following table:

| Bbp variant | Ligand | $K_d$ [nM] |
|---|---|---|
| Bbp: | digoxigenin | —* |
| DigA: | digoxigenin | 295 ± 37 |
|  | digoxin | 200 ± 34 |
| DigA16: | digoxigenin | 30.2 ± 3.6 |
|  | digoxin | 31.1 ± 3.2 |
|  | digitoxigenin | 2.8 ± 2.7 |
|  | digitoxin | 2.7 ± 2.0 |
|  | ouabain | —* |
|  | testosterone | —* |
|  | 4-aminofluroescein | —* |

*no detectable binding activity

Example 4

Preparation of Fusion Proteins of the DigA16 Mutein and Bacterial Alkaline Phosphatase and use for Detecting Digoxigenin Groups in an ELISA and in a Western Blot In order to produce two different fusion proteins of the DigA16 mutein and bacterial alkaline phosphatase (PhoA) with different arrangement of the partners within the polypeptide chain, the two expression plasmids pBBP27 and pBBP29 were constructed by using the molecular-biological methods familiar to the skilled worker.

pBBP27 codes for a fusion protein of PhoA including the signal sequence thereof, a short peptide linker having the amino acid sequence Pro—Pro-Ser-Ala (SEQ ID NO: 29), the sequence corresponding to the mature DigA16 mutein and the Strep-tag-II. A relevant section of the pBBP27 nucleic acid sequence is represented, together with the encoded amino acid sequence, as SEQ ID NO:17 and 26, Respectively, in the sequence listing. The section begins with the XbaI cleavage site and ends with the HindIII cleavage site. The vector elements outside this region are identical to vector pBBP21.

pBBP29 codes for a fusion protein of DigA 16 with preceding OmpA signal sequence, followed by the peptide sequence for Strep-tag II, a sequence of 5 glycine residues and the mature PhoA sequence without the N-terminal amino acid arginine. A relevant section of the pBBP29 nucleic acid sequence is represented, together with the encoded amino acid sequence, as SEQ ID NO:18 and 27, respectively, in the sequence listing. The section begins with the XbaI cleavage site and ends with the HindIII cleavage site. The vector elements outside this region are identical to vector pBBP21.

Figure 2:
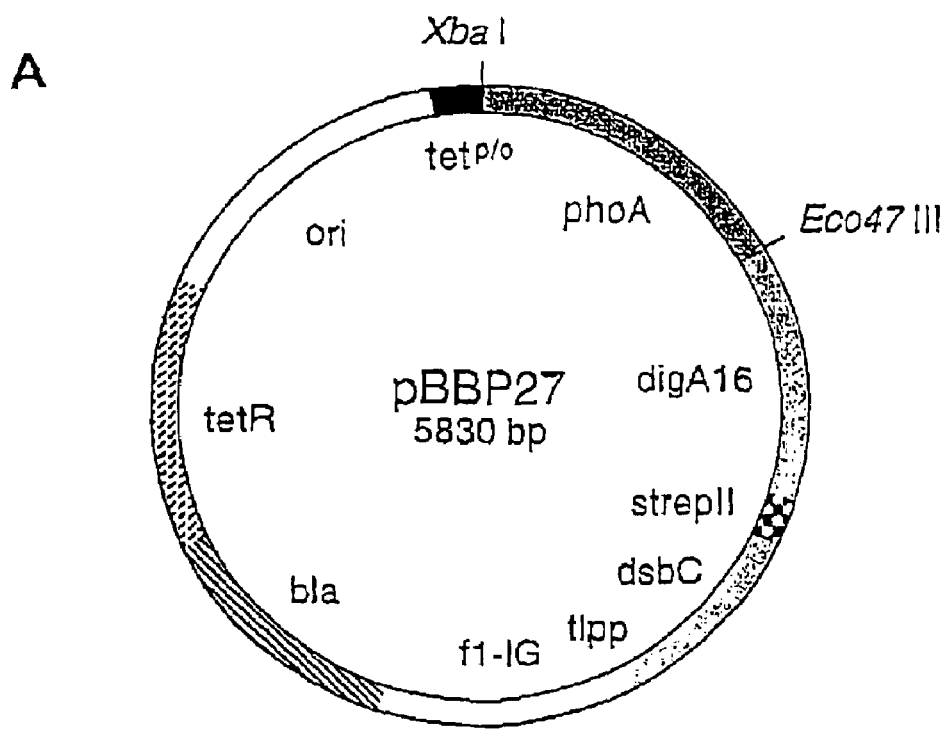
FIG. 2 shows a drawing of the expression vectors pBBP27 (A) and pBBP29 (B). pBBP27 codes for a fusion protein of bacterial alkaline phosphatase with its own signal sequence, a peptide linker having the sequence Pro—Pro-Ser-Ala (SEQ ID NO: 29), the mutein DigA16 and also the Strep-tag II affinity tag. The corresponding structural gene is followed by the dsbC structural gene (including its ribosomal binding site) from E. coli (Zapun et al., Biochemistry 34 (1995), 5075–5089) as second cistron. The artificial operon formed in this way is under joint transcriptional control of the tetracycline promoter/operator (tetp/o) and ends at the lipoprotein transcription terminator (t1pp). Further vector elements are the origin of replication (ori), the intergenic region of filamentous bacteriophage f1(f1—IG), the ampicillin resistance gene (bla) coding for β-lactamase and the tetracycline repressor gene (tetR). pBBP29 codes for a fusion protein of the OmpA signal sequence, the mutein DigA16, the Strep-tag II affinity tag, a peptide linker consisting of five glycine residues, and bacterial alkaline phosphatase without its N-terminal amino acid arginine. The vector elements outside this region are identical to vector pBBP27.
Figure 2:
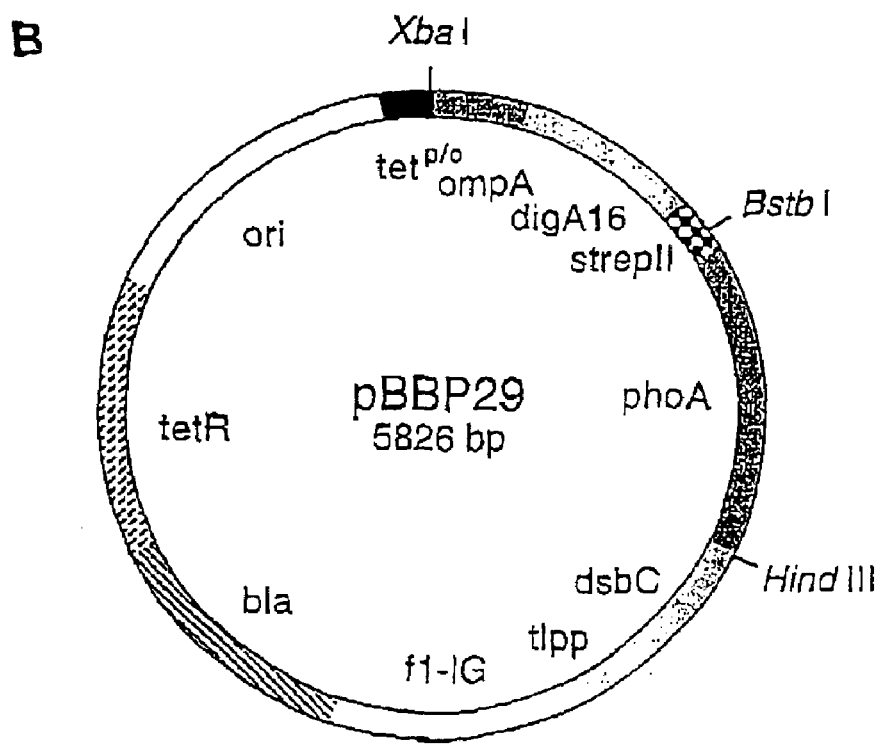

Both plasmids additionally code for the bacterial protein disulfide isomerase DsbC on a separate cistron located in 3' direction. The plasmids are shown diagrammatically in FIG. 2.

The fusion proteins encoded by plasmids pBBP27 and pBBP29 were produced analogously to the method for preparing the simple muteins, described in Example 3. In order to avoid complexing the metal ions from the active center of PhoA, lysis of the bacterial periplasm was carried out using EDTA-free lysis buffer. Polymyxin B sulfate (2 mg/ml, Sigma) was added to the buffer as an agent destabilizing the outer cell membrane. All other buffers used for purification were likewise EDTA-free.

The fusion proteins purified by affinity chromatography by means of the Strep-tag II were dialyzed against PBS buffer overnight. The fusion protein yields were between 100 and 200 μg per 2 l of culture medium. The purity of the fusion proteins obtained was checked by SDS polyacrylamide gel electrophoresis, according to Example 3, and determined to be 90–95%. Subsequently, the fusion proteins were used for directly detecting conjugates of the digoxigenin group with various proteins both in a sandwich ELISA and in a Western blot.

While the conjugates used of digoxigenin with RNaseA and BSA were prepared according to Example 1, a conjugate of digoxigenin with ovalbumin (Sigma) was prepared by adding 1.5 μmol (0.99 mg) DIG-NHS in 25 μl of DMSO in μl steps and with constant mixing to 300 nmol (13.5 mg) of ovalbumin in 1.9 ml of 5% sodium hydrogen carbonate. The mixture was incubated with stirring at RT for 1 h. Excess reagent was removed from the ovalbumin conjugate via a PD-10 gel filtration column according to the manufacturer's instructions.

For detecting digoxigenin groups in a sandwich ELISA, the wells in in each case two rows of a microtiter plate (ELISA strips, 2×8 well with high binding capacity, F-type, Greiner) were filled in each case with 100 μl of a 100 μg/ml solution of the BSA-digoxigenin conjugate or the ovalbumin-digoxigenin conjugate in PBS and incubated at RT overnight. As a control, the wells of a fifth vertical row of the microtiter plate were filled with 100 μl of a 100 μg/ml solution of nonconjugated BSA (Sigma) in PBS and likewise incubated at RT overnight. After removing the solution, unoccupied binding sites were saturated with 200 μl of a solution of 2% w/v BSA in PBST for 2 h. After washing three times with PBST, 50 μl of a 1 μM solution of the purified fusion protein were in each case introduced into the first well of a row, and the Tween concentration was adjusted to 0.1% v/v by adding 1 μl of a solution of 5% v/v Tween. The subsequent wells in each row were initially charged with 50 μl of PBST. Then, 50 μl of the purified fusion protein were pipetted in each case into the second well, mixed and, starting therefrom, 1:2 dilutions were prepared stepwise in the other wells of the vertical row. After incubation at RT for 1 h, the wells were washed twice with PBST and twice with PBS. The fusion proteins bound to the digoxigenin groups were finally detected by means of alkaline phosphatase-catalyzed hydrolysis of p-nitrophenyl phosphate. For this purpose, 100 μl of a solution of 0.5 mg/ml p-nitrophenyl phosphate (Amresco) in AP buffer (100 mM NaCl, 5 mM MgCl$_2$, 100 mM Tris/HCl pH 8.8) were introduced into the wells and product formation was monitored by measuring absorption at 405 nm in a SpectraMax 250 photometer (Molecular Devices).

Figure 3:
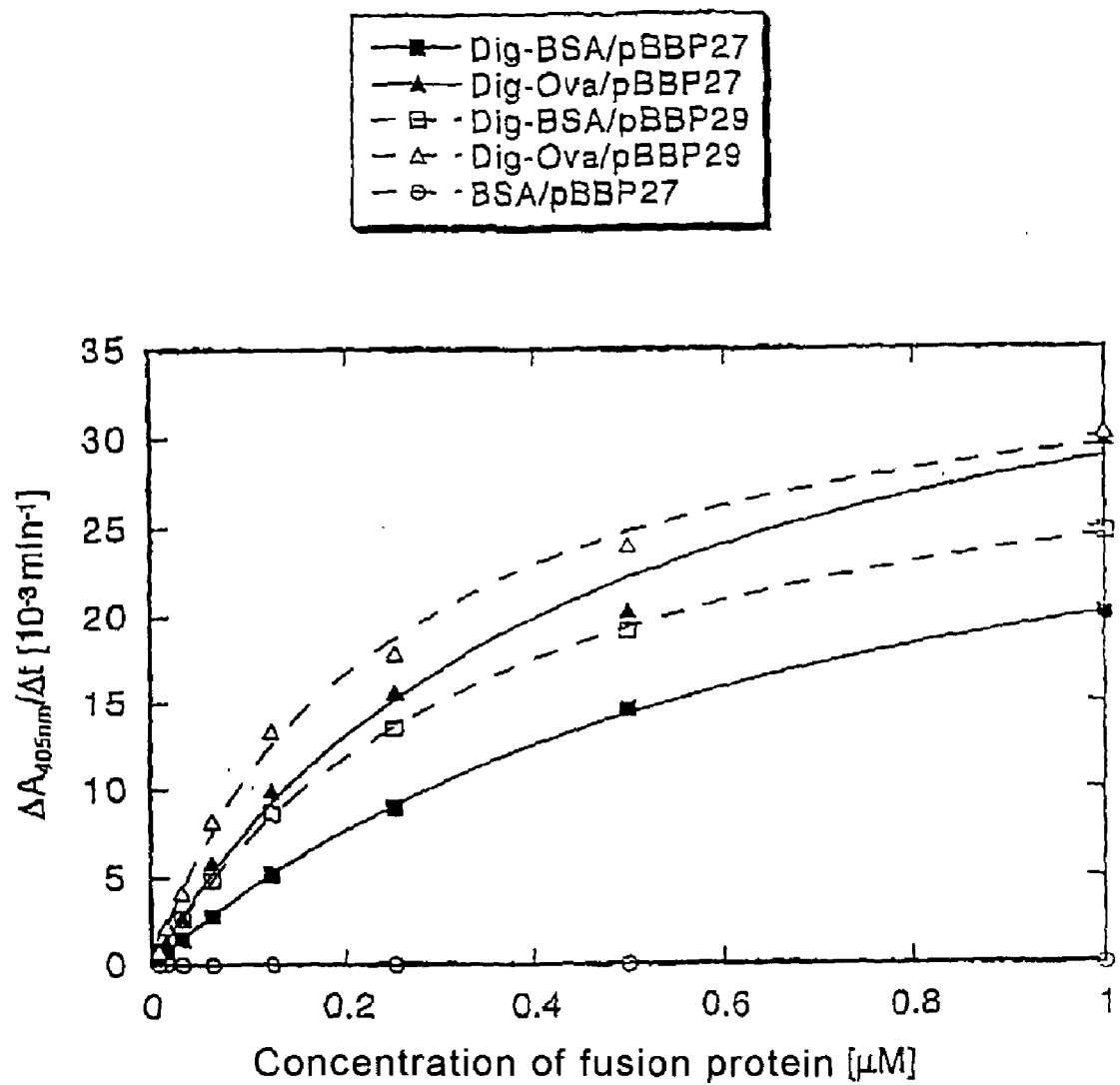
FIG. 3 shows a graphic representation of the data from Example 4 in which digoxigenin groups were detected quantitatively with the aid of mutein DigA16 fusion proteins as gene products of vectors pBBP27 (closed symbols) and pBBP29 (open symbols). Here, the digoxigenin groups were coupled on the one hand to bovine serum albumin (BSA, squares) or, on the other hand, to chicken egg albumin (ovalbumin, triangles) The control data shown are those obtained when using underivatized bovine serum albumin and the fusion protein encoded by pBBP27 (open circles). The enzymatic activity corresponding to the particular bound fusion protein was monitored spectrophotometrically at 405 nm on the basis of p-nitrophenyl phosphate hydrolysis. Curve fitting was carried out by non-linear regression with the aid of the Kaleidagraph computer program (Abelbeck Software) by means of the equation $$[P \cdot L] = [L]_t [P]_t / (K_d + [P]_t)$$

FIG. 3 shows the result of this measurement. According to this, the digoxigenin group is recognized both as conjugate with BSA and as conjugate with ovalbumin, leading to the conclusion that binding by the DigA16 mutein is context-independent. Furthermore, both fusion proteins are active both with regard to the binding function for the digoxigenin group and enzymatically and produce, despite their different structure, almost identical signals.

In order to use the fusion proteins encoded by vectors pBBP27 and pBBP29 in a Western blot, 5 μl of a protein mixture in PBS, whose concentration of digoxigenin-BSA conjugate, digoxigenin-ovalbumin conjugate and digoxigenin-RNaseA conjugate was simultaneously in each case 100 μg/ml, as well as 5 μl of a protein mixture in PBS, whose concentration of underivatized BSA, ovalbumin and RNaseA likewise was simultaneously in each case 100 μg/ml, were first separated by SDS polyacrylamide gel electrophoresis. The protein mixture was then transferred to nitrocellulose by electrotransfer (Blake et al., Anal. Biochem. 136 (1984), 175–179). The membrane was then washed in 10 ml of PBST for three times 5 min and incubated with 10 ml of a 0.5 μM solution of in each case one of the two fusion proteins for 1 h. The membrane was then washed in 10 ml PBST for two times 5 min and in 10 ml of PBS for two times 5 min and finally gently agitated in 10 ml of AP buffer for 10 min. For the chromogenic detection reaction, the membrane was incubated in 10 ml of AP buffer to which 30 μl BCIP (50 μg/ml in dimethylformamide) and 5 μl NBT (75 μg/ml in 70% v/v dimethylformamide) had been added, and bound fusion protein was detected in this way.

FIG. 4 shows the result of this detection method. It turns out again that binding of the digoxigenin group by the two fusion proteins is independent of the carrier protein and that both fusion proteins achieve comparable signal intensities. The same carrier proteins cause no signal whatsoever if they are not conjugated with the digoxigenin group.

What is claimed is:

1. An isolated mutein of the bilin-binding protein of *Pieris brassicae* wherein said mutein
   (a) is able to bind digoxigenin or digoxigenin conjugates,
   (b) does not bind ouabain, testosterone or 4-aminofluorescein and,
   (c) has an amino acid substitution at one or more of the sequence residues 28, 31, 34, 35, 36, 37, 58, 60, 69, 88, 90, 95, 97, 1, 14, 116, 125, and 127 of the wild type bilin binding protein (SEQ ID NO: 28).

2. The mutein according to claim 1, wherein a complex formed between the mutein of the bilin binding protein and digoxigenin has a dissociation constant of 100 nM or less.

3. The mutein according to claim 1, wherein said mutein carries, in comparison with the wild type bilin-binding protein (SEQ ID NO: 28), at least one of the amino acid substitutions selected from the group consisting of Glu(28)→Gln, Lys(31)→Ala, Asn(34)→Asp, Ser(35)→His, Val(36)→Ile, Glu(37)→Thr, Asn(58)→Arg, His(60)→Ser, 11e(69)→Ser, Leu(88)→Tyr, Tyr(90)→Ile, Lys(95)→Gln, Asn(97)→Gly, Tyr (114)→Phe, Lys (116)→Ser, Gln(125)→Met, and Phe(127)→Leu.

4. The mutein according to claim 3, wherein said mutein has the amino acid sequence depicted as SEQ ID NO: 23.

5. The mute in of claim 1, wherein said mutein carries at least one label group, selected from the group consisting of enzymatic label, radioactive label, fluorescent label, chromophoric label, luminescent label, label containing haptens, biotin, metal complexes, metals, and colloidal gold.

6. A fusion protein comprising the mutein of claim 1, wherein a fusion partner of said fusion protein comprises at least one member selected from the group consisting of an enzyme, a protein, a protein domain, a signal sequence and a peptide that facilitates purification and/or detection of said fusion protein and wherein the fusion partner is fused to the amino terminus of the mutein.

7. The fusion protein according to claim 6, further comprising a second fusion partner that is at least one member selected from the group consisting of an enzyme, a protein, a protein domain, a targeting sequence which allows the transport of the fusion protein in a specific cell compartment and a peptide that facilitates purification and/or detection of said fusion protein and wherein this second fusion partner is fused to the carboxy terminus of the mutein of the bilin binding protein.

8. A fusion protein comprising the mutein of claim 1, wherein a fusion partner of said fusion protein is at least one member selected from the group consisting of an enzyme, a protein, a protein domain, a targeting sequence and a peptide that facilitates purification and/or detection of said fusion protein, wherein said targeting sequence allows the transport of the fusion protein into a specific cell, and wherein the fusion partner is fused to the carboxy terminus of the mutein.

9. The fusion protein according to claim 8, further comprising a second fusion partner that is at least one member selected from the group consisting of characterized in that an enzyme, another a protein, or a protein domain, a signal sequence and/or a peptide that facilitates purification and/or detection of said fusion protein and wherein this second fusion partner is fused to the amino terminus of the mutein of the bilin binding protein.

* * * * *

UNITED STATES PATENT AND TRADEMARK OFFICE
Certificate

Patent No. 7,001,882 B1

Patented: February 21, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Arne Skerra, Freising (DE); and Steffen Schlehuber, Freising (DE).

Signed and Sealed this Twenty-seventh Day of October 2009.

ANDREW J. WANG
*Supervisory Patent Examiner*
Art Unit 1656